(12) United States Patent
Anderson et al.

(10) Patent No.: US 6,783,524 B2
(45) Date of Patent: Aug. 31, 2004

(54) ROBOTIC SURGICAL TOOL WITH ULTRASOUND CAUTERIZING AND CUTTING INSTRUMENT

(75) Inventors: Stephen C. Anderson, Northampton, MA (US); Christopher A. Julian, Los Gatos, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 0 days.

(21) Appl. No.: 10/126,499

(22) Filed: Apr. 18, 2002

(65) Prior Publication Data

US 2002/0177843 A1 Nov. 28, 2002

Related U.S. Application Data

(60) Provisional application No. 60/285,485, filed on Apr. 19, 2001.

(51) Int. Cl.[7] .............................................. A61B 18/04
(52) U.S. Cl. ............................................. 606/28; 606/1
(58) Field of Search ........................... 606/1–19, 49–52

(56) References Cited

U.S. PATENT DOCUMENTS

| | | |
|---|---|---|
| 4,038,987 A | 8/1977 | Komiya |
| 4,149,278 A | 4/1979 | Frosch et al. |
| 4,281,447 A | 8/1981 | Miller et al. |
| 4,332,066 A | 6/1982 | Hailey et al. |
| 4,367,998 A | 1/1983 | Causer |
| 4,486,928 A | 12/1984 | Tucker et al. |
| 4,500,065 A | 2/1985 | Hennekes et al. |
| 4,511,305 A | 4/1985 | Kawai et al. |
| 4,512,709 A | 4/1985 | Hennekes et al. |
| 4,706,372 A | 11/1987 | Ferrero et al. |
| 4,710,093 A | 12/1987 | Zimmer et al. |
| 4,744,363 A | 5/1988 | Hasson |
| 4,751,925 A | 6/1988 | Tontarra |

(List continued on next page.)

FOREIGN PATENT DOCUMENTS

| | | |
|---|---|---|
| WO | WO 93/13916 | 7/1993 |
| WO | WO 94/26167 | 11/1994 |
| WO | WO 95/16396 | 6/1995 |
| WO | WO 95/30964 | 11/1995 |
| WO | WO 96/39944 | 12/1996 |
| WO | WO 99/50721 | 10/1999 |

OTHER PUBLICATIONS

Madhani et al., "The black falcon: A teleoperated surgical instrument for minimally invasive surgery" (submitted to IROS 1998) 9 pages total.

(List continued on next page.)

*Primary Examiner*—Roy D. Gibson
*Assistant Examiner*—Pete Vrettakos
(74) *Attorney, Agent, or Firm*—Townsend&Townsend&CrewLLP; Nathan S. Cassell, Esq.

(57) ABSTRACT

A surgical instrument for enhancing robotic surgery generally includes an elongate shaft with an ultrasound probe, an end effector at the distal end of the shaft, and a base at the proximal end of the shaft. The end effector includes an ultrasound probe tip and the surgical instrument is generally configured for convenient positioning of the probe tip within a surgical site by a robotic surgical system. Ultrasound energy delivered by the probe tip may be used to cut, cauterize, or achieve various other desired effects on tissue at a surgical site. In various embodiments, the end effector also includes a gripper, for gripping tissue in cooperation with the ultrasound probe tip. The base is generally configured to removably couple the surgical instrument to a robotic surgical system and to transmit forces from the surgical system to the end effector, through the elongate shaft. A method for enhancing robotic surgery generally includes coupling the surgical instrument to a robotic surgical system, positioning the probe tip in contact with tissue at a surgical site, and delivering ultrasound energy to the tissue.

19 Claims, 28 Drawing Sheets

U.S. PATENT DOCUMENTS

| | | | |
|---|---|---|---|
| 4,766,775 A | | 8/1988 | Hodge |
| 4,793,053 A | | 12/1988 | Zuccaro et al. |
| 4,809,747 A | | 3/1989 | Choly et al. |
| 4,830,569 A | | 5/1989 | Jannborg |
| 4,832,198 A | | 5/1989 | Alikhan |
| 4,837,703 A | | 6/1989 | Kakazu et al. |
| 4,928,546 A | | 5/1990 | Walters |
| 4,943,939 A | | 7/1990 | Hoover |
| 4,979,949 A | | 12/1990 | Matsen, III et al. |
| 4,996,975 A | | 3/1991 | Nakamura |
| 5,018,266 A | | 5/1991 | Hutchinson et al. |
| 5,078,140 A | | 1/1992 | Kwoh |
| 5,143,453 A | | 9/1992 | Weynant |
| 5,154,717 A | | 10/1992 | Matsen, III et al. |
| 5,174,300 A | | 12/1992 | Bales et al. |
| 5,217,003 A | | 6/1993 | Wilk |
| 5,221,283 A | | 6/1993 | Chang |
| 5,236,432 A | | 8/1993 | Matsen, III et al. |
| 5,255,429 A | | 10/1993 | Nishi et al. |
| 5,257,998 A | | 11/1993 | Ota et al. |
| 5,271,384 A | | 12/1993 | McEwen et al. |
| 5,294,209 A | | 3/1994 | Naka et al. |
| 5,305,203 A | | 4/1994 | Raab |
| 5,312,212 A | | 5/1994 | Naumec |
| 5,313,935 A | | 5/1994 | Kortenbach et al. |
| 5,322,055 A | | 6/1994 | Davison et al. |
| 5,343,385 A | | 8/1994 | Joskowicz et al. |
| 5,354,314 A | | 10/1994 | Hardy et al. |
| 5,355,743 A | | 10/1994 | Tesar |
| 5,359,993 A | | 11/1994 | Slater et al. |
| 5,372,147 A | | 12/1994 | Lathrop, Jr. et al. |
| 5,397,323 A | | 3/1995 | Taylor |
| 5,399,951 A | | 3/1995 | Lavallee et al. |
| 5,400,267 A | | 3/1995 | Denen et al. |
| 5,402,801 A | | 4/1995 | Taylor |
| 5,403,319 A | | 4/1995 | Matsen, III et al. |
| 5,417,210 A | | 5/1995 | Funda et al. |
| 5,427,097 A | | 6/1995 | Depp |
| 5,451,368 A | | 9/1995 | Jacob |
| 5,520,678 A | | 5/1996 | Heckele et al. |
| 5,624,398 A | * | 4/1997 | Smith et al. ............. 604/95.01 |
| 5,631,973 A | | 5/1997 | Green |
| 5,649,956 A | * | 7/1997 | Jensen et al. ............... 606/205 |
| 5,695,500 A | | 12/1997 | Taylor et al. |
| 5,697,939 A | | 12/1997 | Kubota et al. |
| 5,762,458 A | | 6/1998 | Wang et al. |
| 5,792,135 A | | 8/1998 | Madhani et al. |
| 5,797,900 A | | 8/1998 | Madhani et al. |
| 5,800,423 A | | 9/1998 | Jensen |
| 5,808,665 A | | 9/1998 | Green |
| 5,845,646 A | * | 12/1998 | Lemelson ................... 128/899 |
| 5,876,325 A | | 3/1999 | Mizuno et al. |
| 6,056,735 A | * | 5/2000 | Okada et al. .................. 606/1 |
| 6,058,323 A | * | 5/2000 | Lemelson ................... 600/408 |
| 6,066,151 A | | 5/2000 | Miyawaki et al. |
| 6,096,033 A | * | 8/2000 | Tu et al. ....................... 606/31 |
| 6,129,735 A | * | 10/2000 | Okada et al. ............... 606/169 |
| 6,132,368 A | | 10/2000 | Cooper |
| 6,139,561 A | | 10/2000 | Shibata et al. |
| 6,165,191 A | | 12/2000 | Shibata et al. |
| 6,193,709 B1 | | 2/2001 | Miyawaki et al. |
| 6,280,407 B1 | | 8/2001 | Manna et al. |
| 6,319,227 B1 | * | 11/2001 | Mansouri-Ruiz ......... 604/95.01 |
| 6,331,181 B1 | | 12/2001 | Tierney et al. |
| 6,394,998 B1 | | 5/2002 | Wallace et al. |
| 6,454,717 B1 | * | 9/2002 | Pantages et al. ............ 600/466 |
| 6,491,701 B2 | * | 12/2002 | Tierney et al. .............. 606/130 |

OTHER PUBLICATIONS

Moyer, T.H., Thesis entitled "The design of an integrated hand and wrist mechanism" for Master of Science in Mechanical Engineering at the Massachusetts Institute of Technology (1992) pp. 1–106.

Neisius et al., "Robotic manipulator for endoscopic handling of surgical effectors and cameras" Proceedings of the First International Symposium on Medical Robotics and Computer Assisted Surgery, vol. 2, Workshop (Part I & II)–Session VI, pp. 169–175.

Salisbury, J.K., "Kinematic and force analysis of articulated hands" Department of Computer Science, Stanford University, Report No. STAN–CS–89–921 (1982) Chapter 9, pp. 67–77.

Thring, "Robots and telechirs: Manipulators with memory; remote manipulators; machine limbs for the handicapped" (1993) M.W. Thring/Ellis Horwood Ltd. pp. 9–11, 122–131, 194–195, 235–257, 274–279.

* cited by examiner

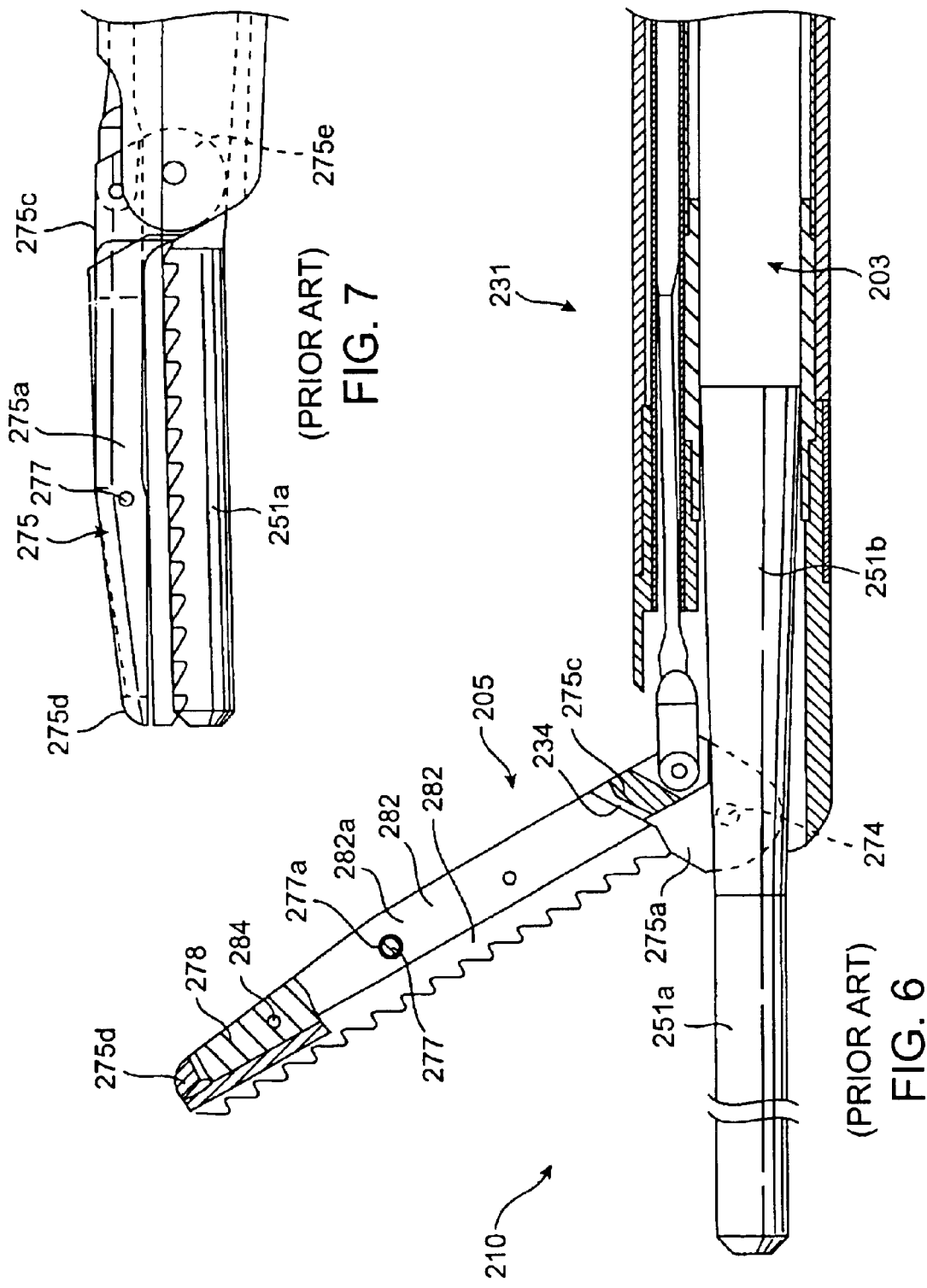

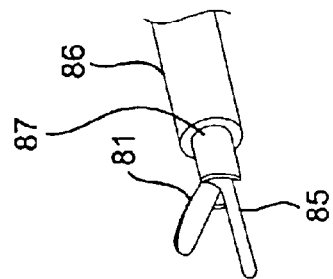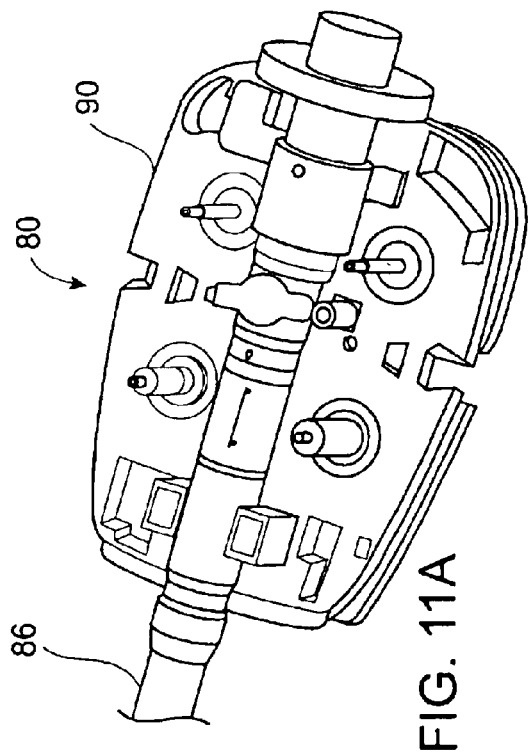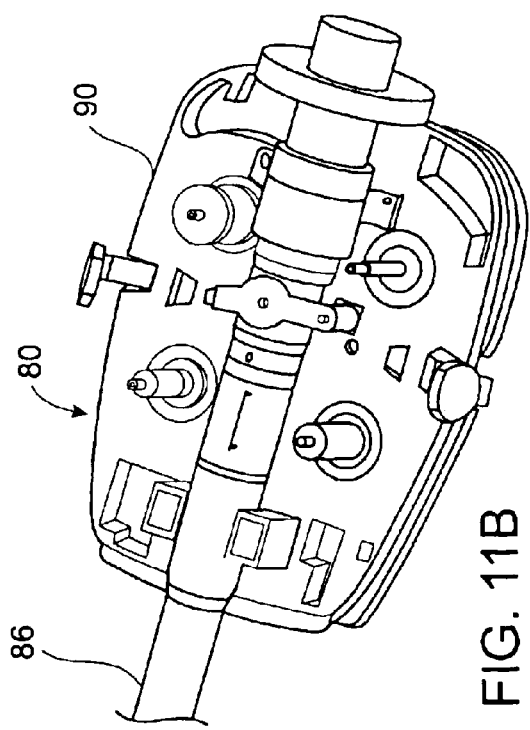

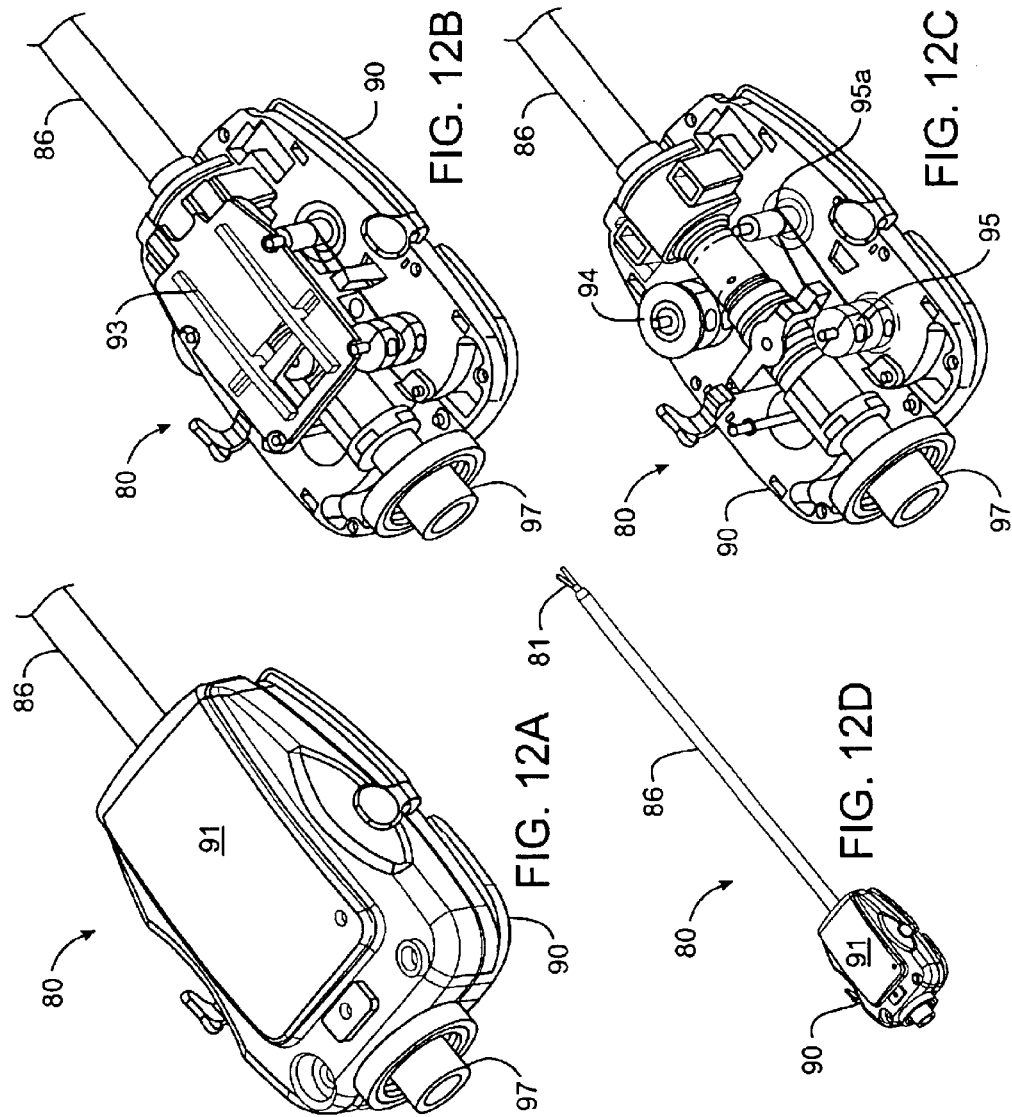

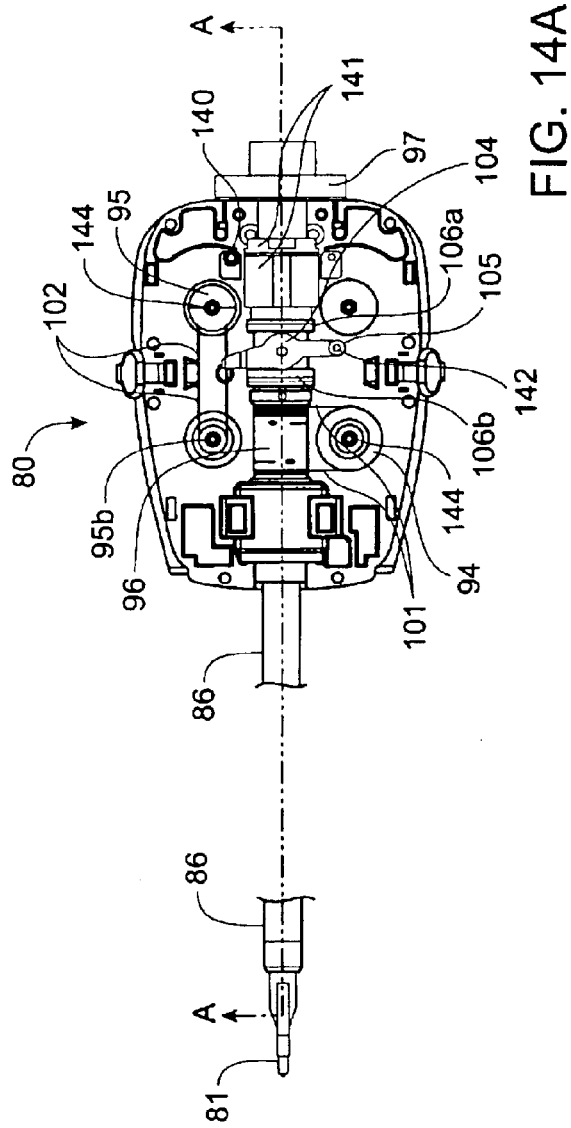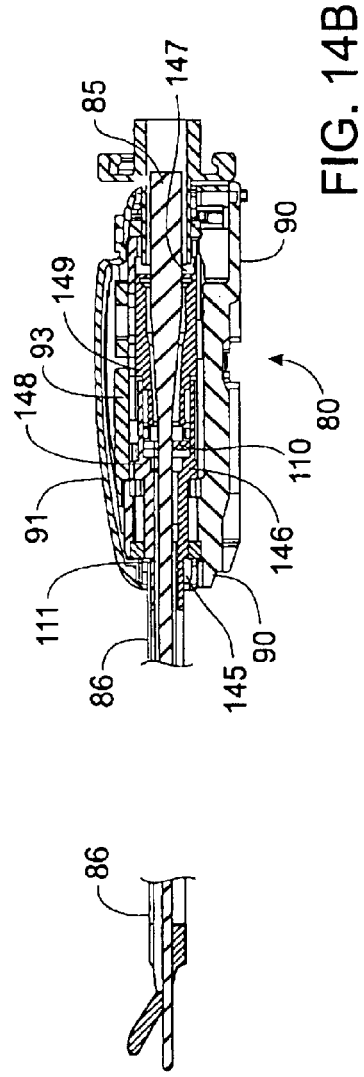
FIG. 14A
FIG. 14B

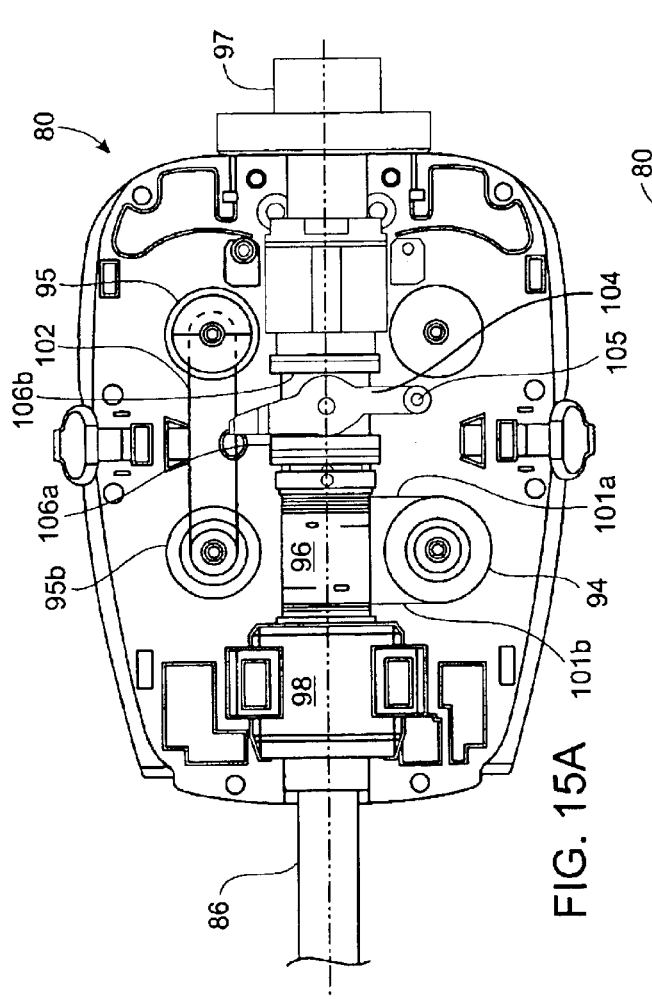
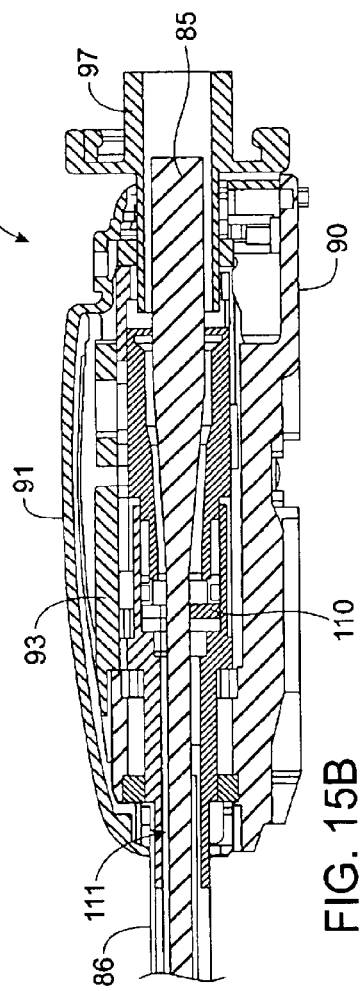
FIG. 15A
FIG. 15B

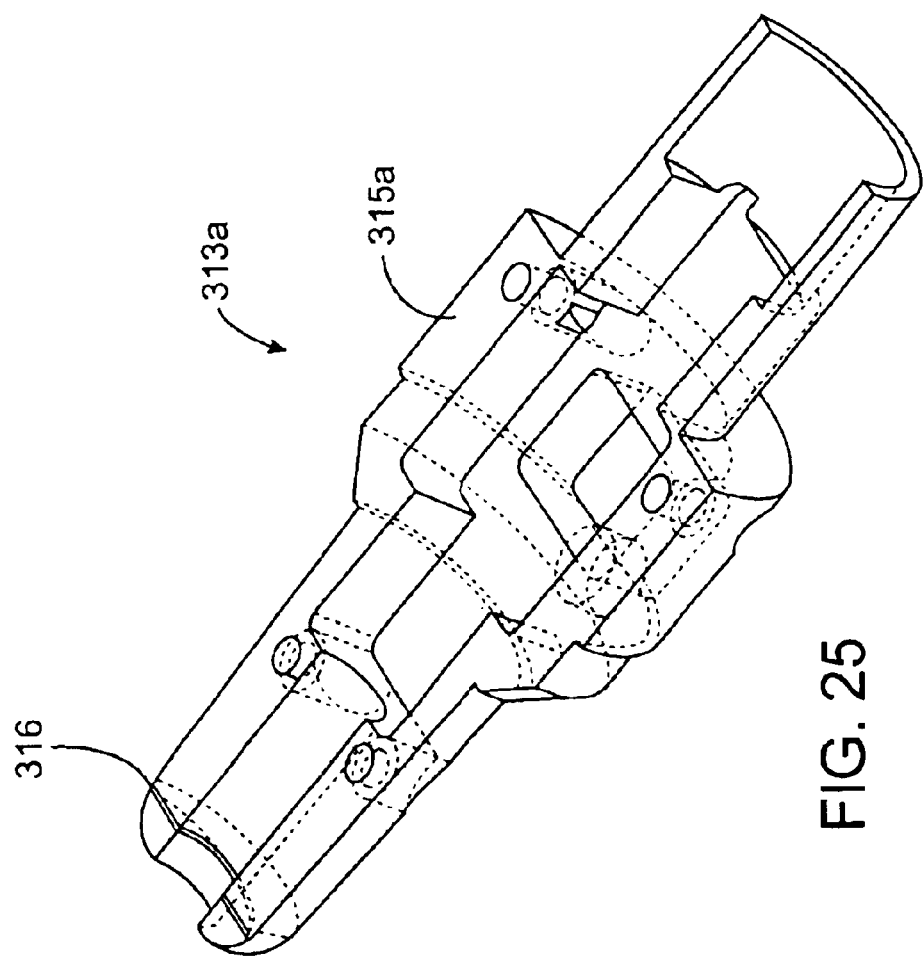

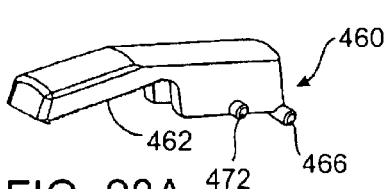
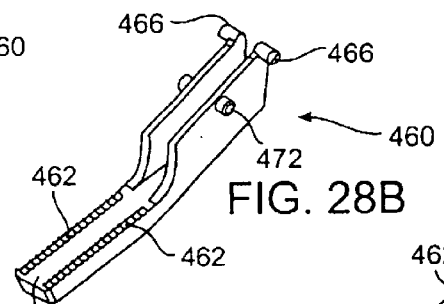
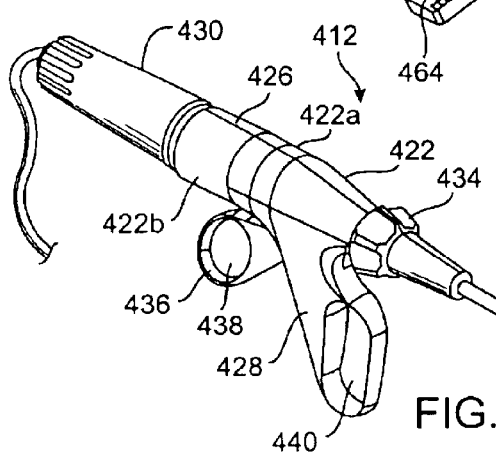
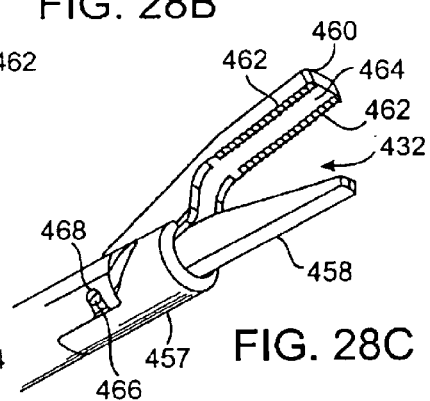
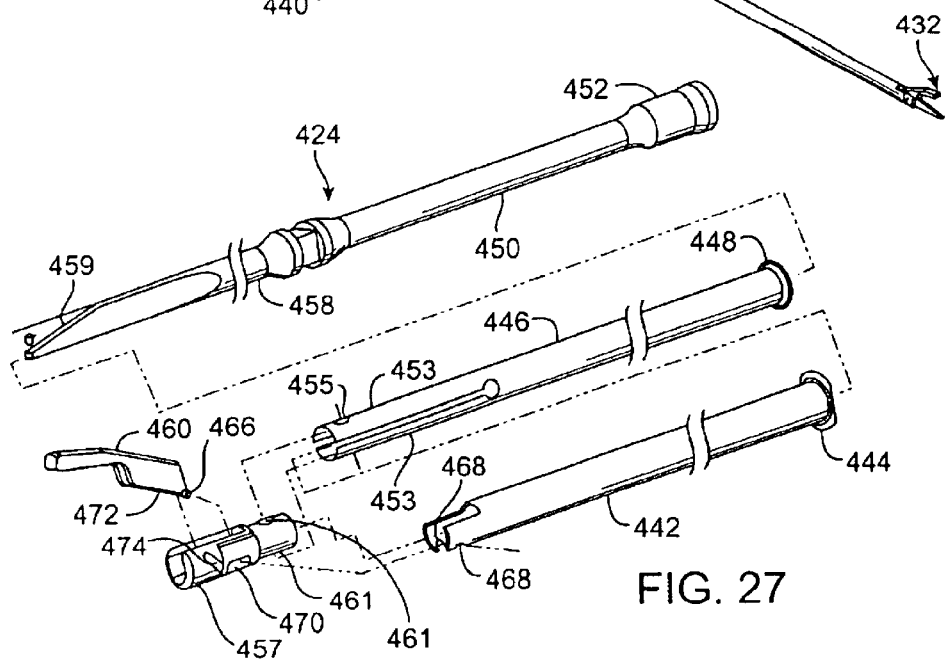

ROBOTIC SURGICAL TOOL WITH ULTRASOUND CAUTERIZING AND CUTTING INSTRUMENT

CROSS-REFERENCES TO RELATED APPLICATIONS

This application claims the benefit of prior provisional application No. 60/285,485, filed on Apr. 19, 2001, under 37 CFR §1.78(a)(4), the full disclosure of which is incorporated herein by reference.

BACKGROUND OF THE INVENTION

The present invention generally relates to surgical apparatus and methods. More specifically, the invention relates to a surgical instrument and method for use with a robotic surgical system, the instrument including an ultrasonic probe.

Minimally invasive surgical techniques generally reduce the amount of extraneous tissue damage during surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. Patient recovery times, patient discomfort, surgical side effects, and time away from work can also be reduced by increasing the use of minimally invasive surgery.

In theory, a significant number of surgical procedures could potentially be performed by minimally invasive techniques to achieve the advantages just described. Only a small percentage of procedures currently use minimally invasive techniques, however, because certain instruments, systems and methods are not currently available in a form for providing minimally invasive surgery.

Traditional forms of minimally invasive surgery typically include endoscopy, which is visual examination of a hollow space with a viewing instrument called an endoscope. One of the more common forms of endoscopy is laparoscopy, which is visual examination and/or treatment of the abdominal cavity. In traditional laparoscopic surgery a patient's abdominal cavity is insufflated with gas and cannula sleeves are passed through small incisions in the musculature of the patient's abdomen to provide entry ports through which laparoscopic surgical instruments can be passed in a sealed fashion. Such incisions are typically about ½ inch (about 12 mm) in length.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by a long extension tube, typically of about 12 inches (about 300 mm) in length, for example, so as to permit the surgeon to introduce the end effector to the surgical site and to control movement of the end effector relative to the surgical site from outside a patient's body.

To perform a surgical procedure, a surgeon typically passes the working tools or instruments through the cannula sleeves to the internal surgical site and manipulates the instruments from outside the abdomen by sliding them in and out through the cannula sleeves, rotating them in the cannula sleeves, levering (i.e., pivoting) the instruments against the abdominal wall and actuating the end effectors on distal ends of the instruments from outside the abdominal cavity. The instruments normally pivot around centers defined by the incisions which extend through the muscles of the abdominal wall. The surgeon typically monitors the procedure by means of a television monitor which displays an image of the surgical site captured by the laparoscopic camera. Typically, the laparoscopic camera is also introduced through the abdominal wall so as to capture the image of the surgical site. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Although traditional minimally invasive surgical instruments and techniques like those just described have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased use of minimally invasive surgery.

Minimally invasive robotic (or "telesurgical") surgical systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

Typically, such a telesurgery system can be provided with at least two master control devices (one for each of the surgeon's hands), which are normally operatively associated with two robotic arms on each of which a surgical instrument is mounted. Operative communication between master control devices and associated robotic arm and instrument assemblies is typically achieved through a control system. The control system typically includes at least one processor which relays input commands from the master control devices to the associated robotic arm and instrument assemblies and from the arm and instrument assemblies to the associated master control devices in the case of, e.g., force feedback, or the like. One example of a robotic surgical system is the DAVINCI™ system available from Intuitive Surgical, Inc. of Mountain View, Calif.

Just as robotic surgical systems have been found advantageous, so too has use of ultrasound energy in surgery been found beneficial. A number of patents disclose ultrasonic treatment instruments for both open surgery and manually-performed endoscopic surgery. These patents include U.S. Pat. No. 6,056,735 issued May 2, 2000, entitled Ultrasound Treatment System; U.S. Pat. No. 6,066,151 issued May 23, 2000, entitled Ultrasonic Surgical Apparatus; U.S. Pat. No. 6,139,561 issued Oct. 31, 2000, entitled Ultrasonic Medical Instrument; U.S. Pat. No. 6,165,191 issued Dec. 26, 2000, entitled Ultrasonic Treating Tool; and U.S. Pat. No. 6,193,709 issued Feb. 27, 2001, entitled Ultrasonic Treatment Apparatus. The full disclosure of each of these patents is incorporated herein by reference.

A typical ultrasound treatment instrument for manual endoscopic surgery is the SonoSurg® instrument model T3070 made by Olympus Optical Co., Ltd., of Tokyo, Japan. Other examples of manually operated ultrasound treatment instruments are the Harmonic Scalpel® LaparoSonic® Coagulating Shears, made by Ethicon Endo-Surgery, Inc, of Cincinnati, Ohio.; and the AutoSonix® Ultra Shears® made by United States Surgical Corporation of Norwalk, Conn. Such an ultrasound treatment instrument may comprise ultrasonic transducers for generating ultrasonic vibrations; a handpiece including the ultrasonic transducers and serving as an operation unit; a generally elongate probe connected to the ultrasonic transducers and serving as a vibration conveyer for conveying ultrasonic vibrations to a distal end effector member or tip used to treat a living tissue; a sheath serving as a protective member for shielding the probe. The instrument typically includes a movable holding, grasping or gripping end effector member pivotally opposed to the distal tip and constituting a movable section which clamps a living tissue in cooperation with the distal tip; an operating mechanism for moving the grasping member between a closed position in which the grasping member engages the distal tip of the vibration transmitting member and an open position in which the grasping member is separated from distal tip portion. The operating mechanism includes handle portions for manipulation and actuation by a surgeon's hands.

Surgical ultrasound instruments are generally capable of treating tissue with use of frictional heat produced by ultrasonic vibrations. For example, the heat may be use to cut and/or cauterize tissue. With many currently available instruments, tissue may first be grasped by an ultrasound surgical device and then ultrasound energy may be delivered to the tissue to cut, cauterize or the like. Ultrasound instruments provide advantages over other cutting and cauterizing systems, such as reduced collateral tissue damage, reduced risk of unwanted burns, and the like. Currently, however, ultrasound instruments for use with a robotic surgical system are not available.

Therefore, a need exists for a surgical instrument, for use with a robotic surgical system, that provides ultrasound energy at a surgical site. Such an instrument would allow the advantages of ultrasound and minimally invasive robotic surgery to be combined.

BRIEF SUMMARY OF THE INVENTION

Surgical apparatus and methods for enhancing robotic surgery generally include a surgical instrument with an elongate shaft having an ultrasound probe, an end effector at the distal end of the shaft, and a base at the proximal end of the shaft. The end effector includes an ultrasound probe tip and the surgical instrument is generally configured for convenient positioning of the probe tip within a surgical site by a robotic surgical system. Ultrasound energy delivered by the probe tip may be used to cut, cauterize, or achieve various other desired effects on tissue at a surgical site. By providing ultrasound energy via a robotic surgical instrument for use with a robotic surgical system, the apparatus and methods of the present invention enable the advantages associated with ultrasound to be combined with the advantages of minimally invasive robotic surgery.

In accordance with one aspect, the present invention provides a method of performing a robotic surgical procedure on a patient. Generally, the method includes coupling a surgical instrument with a robotic surgical system, the surgical instrument having a distal end with an ultrasound probe tip, positioning with the robotic surgical system the ultrasound probe tip in contact with tissue at a surgical site in the patient, and delivering ultrasound energy to the tissue with the ultrasound probe tip. Optionally, the distal end of the surgical instrument further includes a gripping member. In embodiments including a gripping member, the method further includes transmitting at least one force from the robotic surgical system to the gripping member and moving the gripping member with the at least one force to hold a portion of the tissue between the gripping member and the ultrasound probe tip.

In some embodiments, the method further includes transmitting the at least one force from an interface member on the robotic surgical system to a first rotatable shaft on the surgical instrument, the first rotatable shaft being coupled to a second rotatable shaft by a cable, the cable being coupled to an actuator rod, and the actuator rod being coupled to the gripping member, wherein the at least one force causes the first shaft, the second shaft and the cable to rotate, causing the actuator rod to move the gripping member. In other embodiments, the method further includes releasing the portion of tissue after delivering a desired amount of ultrasound energy to the portion of tissue. In various embodiments, the method also includes using the ultrasound probe tip to cut the tissue, cauterize the tissue, or both.

In another aspect, the present invention provides a surgical instrument for use with a robotic surgical system. Generally, the surgical instrument includes an elongate shaft having a proximal end and a distal end, the elongate shaft including an ultrasound probe, an end effector disposed at the distal end, the end effector including an ultrasound probe tip of the ultrasound probe, and a base disposed at the distal end for connecting the surgical instrument to the robotic surgical system. Optionally, the elongate shaft may be configured to rotate in relation to the base about an axis drawn from the proximal end to the distal end.

Also optionally, the base of the surgical instrument may include: at least two shafts rotatably mounted within the base, each of the shafts having two ends, at least one of the ends of one of the shafts protruding from the base to engage a corresponding interface member on the robotic surgical system; at least two spools, each spool being mounted on one of the shafts; at least one cable for connecting two of the spools; and a rotating member coupled to the cable and to the elongate shaft, the rotating member being configured to rotate the elongate shaft in response to movements of the interface member, the at least two shafts, the at least two spools and the at least one cable.

In some embodiments, the end effector of the surgical instrument includes a gripping member hingedly attached to the end effector for gripping tissue in cooperation with the ultrasound probe tip. In those embodiments, the surgical instrument may optionally include at least one force transmitting member for transmitting one or more forces between the robotic surgical system and the gripping member to move the gripping member. In various embodiments, the transmitting member may include: at least two shafts rotatably mounted within the base, each of the shafts having two ends, at least one of the ends of one of the shafts protruding from the base to engage a corresponding interface member on the robotic surgical system; at least two spools, each spool being mounted on one of the shafts; at least one cable for connecting two of the spools; and an actuator rod coupled to the cable and to the gripping member and extending through the elongate shaft, the actuator rod being configured to move the gripping member in response to movements of the interface member, the at least two shafts, the at least two spools and the at least one cable.

In some embodiments, the base of the surgical instrument includes an ultrasound source connector for connecting the ultrasound probe to an external ultrasound source. In other embodiments, the base includes an internal ultrasound source for providing ultrasound energy to the ultrasound probe.

Generally, the ultrasound probe of the surgical instrument may include various components. For example, in one embodiment the probe includes an ultrasound transducer for generating ultrasonic vibrations and one or more amplifying horns for amplifying the ultrasonic vibrations.

In some embodiments, the ultrasonic probe assembly may be arranged to be axially movable within the elongate shaft, and the proximal portion of the probe may be mechanically coupled to one or more movable interface members so that the probe is movable in a reciprocating manner in response to movement of the interface member. The distal portion of the probe assembly may be coupled to the grip member, so that the grip opens or closes as the probe moves axially. In this manner the movable probe assembly may serve the function of a grip actuator rod in addition to transmitting ultrasound energy to the surgical site.

Certain exemplary surgical instrument embodiments having aspects of the invention may be described or characterized in general terms as comprising an instrument probe assembly having a distal end configured to be insertable into a patient's body through a small aperture, such as a minimally invasive surgical incision or the like, typically defined by a cannula or trocar. The instrument probe assembly comprises a proximal end coupled to an instrument base. The instrument probe assembly typically is elongate, having an axis extending between the distal and proximal probe ends, and may have a generally straight or shaft-like medial portion. In alternative embodiments, the medial probe portion may be curved and/or may be flexible in shape relative to the axis. The instrument base includes an instrument interface assembly which is engagable to a robotic surgical system. Preferably, the instrument interface assembly is removably engageable to the robotic surgical system, and may include a latch mechanism permitting quick connection and disconnection.

The instrument interface assembly is engagable with provides for one or more instrument actuation inputs from the robotic surgical system in response to an input by an operator (i.e., an activation input to the instrument, being an activation output from the robotic surgical system, which in turn is a response by the robotic control system to an operator control input). Preferably the one or more instrument activation inputs include an input to activate at least one degree of freedom of motion of the all or a portion of the instrument probe assembly relative to the instrument base. The activation input may be a mechanical input, an electrical input, a magnetic input, a signal input, an optical input, a fluidic input, a pneumatic input, and the like, or a combination of these, without departing from the spirit of the invention.

In certain exemplary embodiments of surgical instruments having aspects of the invention, at least one activation input includes an operative engagement of a rotatable interface body (activation interface body) of the robotic surgical system with a corresponding rotatable shaft (instrument interface body or instrument interface shaft) of the instrument interface assembly in the instrument base. The rotatable shaft is in turn mechanically coupled by one or more drive elements to all or a portion of the to the instrument probe assembly, so as to impart a corresponding degree of freedom to all or a portion of the instrument probe assembly relative to the base.

As described above, in alternative embodiments another type of activation modality may be substituted for the rotatable interface body of the robotic surgical system. For example, an electrical power/control interface (e.g., including a multi-pin connector) may be included in the interface assembly to transmit electrical power and/or control signals from the robotic surgical system to actuate a motor pack mounted in the instrument base, the motor pack output may in turn may be coupled to the instrument probe assembly so as to impart one or more corresponding degrees of freedom to all or portions of the instrument probe assembly relative to the base. The motor pack may include one or more electrical motors, transmission gearing, position encoders, torque sensors, feedback sensors, and the like, and may transmit feedback or sensor signals to the robotic surgical system via the interface.

In certain exemplary embodiments of surgical instruments having aspects of the invention, the at least one degree of freedom of motion in response to an activation input from the robotic surgical system includes the pivotal activation of a clamp or grip member of an end effector coupled to the distal probe end. In certain exemplary embodiments, the at least one degree of freedom of motion includes the axial rotation of at least the major portion of the instrument probe assembly about its axis relative to the instrument base.

In alternative embodiments other types of degrees of freedom of motion of all or a portion of the instrument probe assembly may be activated by engagement of the robotic surgical system. For example, the instrument probe assembly may include at least one distal joint to controllably orient the distal probe end relative to the probe axis, such as a wrist-like rotational or pivotal joint supporting a distal end effector. In another example, the probe medial portion may have a flexible section which is controllably variable in shape by one or more degrees of freedom, being driveable by longitudinal tendon members extending within the instrument probe assembly.

In these alternative embodiments, the instrument interface assembly is coupled to drive members of the instrument probe assembly to activate such degrees of freedom and is engagable with the robotic surgical system to receive activation inputs to activate such drive members. Further examples of alternative instrument embodiments include instrument probe assemblies having controllable shape-memory components, movable piezo-electric drive elements, hydraulic drive elements, and the like, or combinations of these. As describe above, the robotic activation input may include a corresponding activation modality suitable for any of these instrument probe assembly movement modalities, without departing from the spirit of the invention.

To reduce costs and for manufacturing convenience, the instrument may include OEM parts. For example, the instrument probe assembly may include parts or components generally similar or identical to parts or components (OEM components) of current or future commercially-available endoscopic instruments for surgical or diagnostic uses (OEM medical systems), including manually operated instruments. The surgical instruments of the invention may perform some or all of the functions of such OEM medical systems. For example, the instrument probe assembly of the surgical instruments of the invention may include OEM components of ultrasound treatment probes, electrocautery probes, ultrasound diagnostic probes, diagnostic imagery probes. In further examples, the instrument probe assembly may include suitable OEM components of biopsy probes, suction probes, substance injection probes, surgical accessory application probes, stapler probes, tissue grasping and cutting probes, and the like. Likewise, the instrument probe assembly may combine more than one of the medical functions of the above described instruments.

In certain exemplary embodiments of surgical instruments having aspects of the invention, the instrument probe assembly comprises a distally disposed end effector coupled to the probe distal end to engage tissue employing a medical energy modality. For example, the instrument probe assembly may include a conduction element or conduction core coupled to the end effector; and extending along the probe axis. The conduction element may be configured and composed to communicate the medical energy between the end effector and a medical energy source. For example, the instrument may include one or more energy connector devices coupled to the conduction element, the connector devices being engagable operatively communicate to a power, signal and/or control system external to the instrument to enable medical functions of the instrument (medical energy system).

The medical energy system may include a power, signal and/or control system which is distinct from the robotic surgical system, such as the power, signal and/or control system of an OEM medical system. Such medical energy systems may likewise be responsive to a control input of an operator. For example, instrument embodiments of the invention may include a cable connector configured to connect to an OEM surgical ultrasound generator, an OEM electrocautery generator, and the like.

Optionally, the energy connector device of the instrument may be configured for "wireless" engagement with the medical energy system, so that operative reception and/or transmission of the medical energy signal may be by non-contact communication with the medical energy system.

In a further option, the medical energy system may be integrated with the robotic surgical system. Optionally, the respective energy connector devices may be integrated with the instrument interface assembly, and optionally operator input devices of the medical energy system may be integrated with the operator input devices of the robotic surgical system.

In the particular instrument examples shown in the figures, the medical energy modality is ultrasound energy for tissue treatment, and the instrument probe assembly comprises an ultrasonic treatment assembly or ultrasonic treatment probe. The ultrasonic treatment probe includes a transducer coupled to an ultrasonic acoustical conduction core, the transducer preferably being supported at least partially by the instrument base. The medical energy system comprises an OEM ultrasonic generator. The interface connector device includes a cable connector mounted to the base and engagable with a cable to communicate with an OEM ultrasonic generator. The ultrasonic treatment probe includes a probe tip coupled to the conduction core and configured to engage tissue and controllably transmit ultrasound energy to the engaged tissue.

As described above, in alternative embodiments an instrument probe assembly employing another type of medical energy modality may be included. For example, the instrument probe assembly may comprise an electrosurgical treatment probe including a electrical conduction element coupled to an end effector, and the base may include a connector interface coupled to the electrocautery treatment probe, and configured to be connectable to an OEM electrosurgical generator. In further examples, the instrument probe assembly may include a conduction element for communicating a diagnostic energy modality, e.g., signals to and/or from an end effector having an diagnostic ultrasound transducer or other diagnostic sensor and or transmitter.

BRIEF DESCRIPTION OF THE DRAWINGS

FIG. 6 is a side-view illustration of the distal end of a manually operated ultrasound treatment apparatus as in FIGS. 4 and 5, with a jaw of the distal end in an open position.

FIG. 7 is a side-view illustration of the distal end of a manually operated ultrasound treatment apparatus as in FIGS. 4 and 5, with a jaw of the distal end in a closed position.

FIGS. 11a–b are perspective illustrations of a proximal portion of a surgical tool according to an embodiment of the present invention, with a cover on a tool base of the surgical tool removed to show internal structures of the tool base.

FIG. 11c is a perspective illustration of a distal portion of a robotic surgical tool according to an embodiment of the present invention.

FIG. 12a is a perspective illustration of a proximal portion of a surgical tool according to an embodiment of the present invention, including a tool base of the surgical tool.

FIG. 12b is a perspective illustration of a proximal portion of a surgical tool as in FIG. 12a, with a cover on the tool base removed to show internal structures of the tool base.

FIG. 12c is a perspective illustration of a proximal portion of a surgical tool as in FIG. 12b, with a an upper chassis further removed from the tool base to show internal structures of the tool base.

FIG. 12d is a perspective illustration of a surgical tool according to an embodiment of the present invention.

FIG. 14a is a top-view illustration of a tool base as shown in FIGS. 12c and 13.

FIG. 14b is a side-view illustration of a tool base according to an embodiment of the present invention.

FIG. 15a is an enlarged view of a tool base as shown in FIG. 14a.

FIG. 15b is an enlarged view of a tool base as shown in FIG. 14b.

FIG. 25 is a perspective view of a molded half portion of the adaptor housing of the removable treatment assembly shown in FIGS. 21 and 22.

FIG. 26 is a side perspective view of another alternate embodiment of an ultrasonic instrument in an open position, as described in U.S. Pat. No. 6,280,407.

FIG. 27 is a perspective view of an elongated body portion of the ultrasonic instrument shown in FIG. 26.

FIG. 28A is a side perspective view of the clamp of the ultrasonic instrument shown in FIG. 26.

FIG. 28B is a side perspective view of the tissue contact surface of the clamp shown in FIG. 28A.

FIG. 28C is a side perspective view of the distal end of the elongated body portion of the ultrasonic instrument shown in FIG. 26.

DETAILED DESCRIPTION OF THE INVENTION

The present invention provides robotic surgical apparatus and methods for applying ultrasound energy in robotic surgery. In various embodiments, the invention includes a robotic surgical apparatus for use with a robotic surgical system. The apparatus typically includes an elongate shaft with an end effector at one end and a base at the opposite end. In some embodiments, the end effector includes an ultrasound tip and a gripper for gripping tissue and the like between the gripper and the ultrasound tip. Optionally, the gripper may also pivot around one or more axes in relation to the apparatus. The tool base is generally configured to engage the robotic surgical system and to transmit forces from the robotic surgical system to the gripper, for example to pivot the gripper. Use of ultrasound in robotic surgery, as provided by apparatus and methods of the present invention, will allow for more precise, safe cutting and cauterization of tissues as well as other advantages typically seen with ultrasound.

Figure 1:
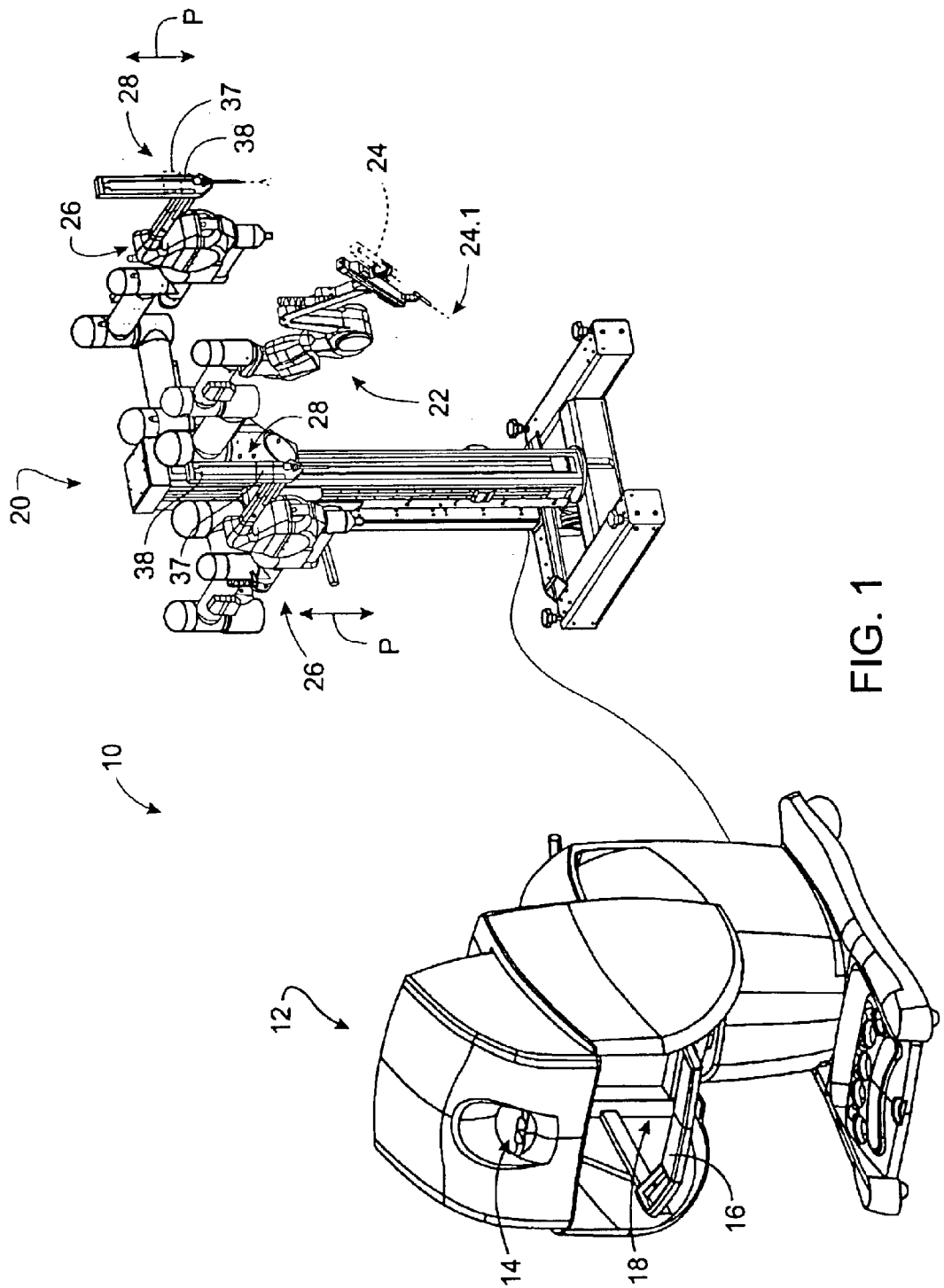
FIG. 1 is a perspective illustration of a robotic surgical system with which various embodiments of the present invention may be used.

Referring now to FIG. 1, a robotic surgical system 10 suitably includes a user-operated control station 12 and a surgical work station, or "cart" 20. The control station 12 includes an image display module 14 for displaying an image of a surgical site, a support 16 on which an operator may rest his/her forearms, and a space 18 where two master control devices are located (not shown). When using control station 12, a surgeon or other user typically sits in a chair in front of control station 12, positions views the surgical site through display module 14 and grips the master controls one in each hand while resting the forearms on support 16. One example of a robotic surgical system as described in FIG. 1 is the DAVINCI™ system available from Intuitive Surgical, Inc. of Mountain View, Calif.

Control station 12 is generally coupled to cart 20 such that command from master controls may be transmitted to cart 20. In use, cart 20 is positioned adjacent a patient requiring surgery and is then normally caused to remain stationary until a surgical procedure to be performed by means of surgical system 10 is complete. Cart 20 typically has wheels or castors to render it mobile. Control station 12 is typically positioned remote from cart 20 and in some embodiments may be separated from cart 20 by a great distance, for example miles away, but will typically be used within an operating room with cart 20.

In various embodiments, cart 20 includes at least three robotic arm assemblies 22, 26, 26, one of which is configured to hold an image capture device 24 and the others of which are configured to hold surgical instruments 28. Alternatively, cart may include more or fewer than three robotic arm assemblies and the robotic arm assemblies may be configured to hold any suitable tool, instrument, imaging device and/or the like. Image capture device 24 may include any suitable device, such as an endoscope, fiber optic camera, or the like. Image capture device 24 generally includes an object viewing end 24.1 at a remote end of an elongate shaft configured to enable viewing end 24.1 to be inserted through an entry port in a patient's body to capture an image of a surgical site. Coupling of cart 20 to control station 12 generally enables display module 14 to display an image captured by image capture device 24.

Coupling of cart 20 to control station 12 also typically allows each of master controls on control station 12 (not shown) to control one robotic arm assembly 26 and one surgical instrument 28. In various embodiments, each master control may alternatively be used to control more than one robotic arm assembly 26 and/or more than one surgical instrument 28.

Surgical instruments 28 on the robotic arm assemblies 26 typically include elongate shafts, with proximal and distal ends. End effectors are generally mounted on wrist-like mechanisms pivotally mounted on the distal ends of the shafts, for enabling the instruments 28 to perform one or more surgical tasks. Generally, the elongate shafts of surgical instruments 28 allow the end effectors to be inserted through entry ports in a patient's body so as to access the internal surgical site. Movement of the end effectors is generally controlled via master controls on control center 12.

Figure 2:
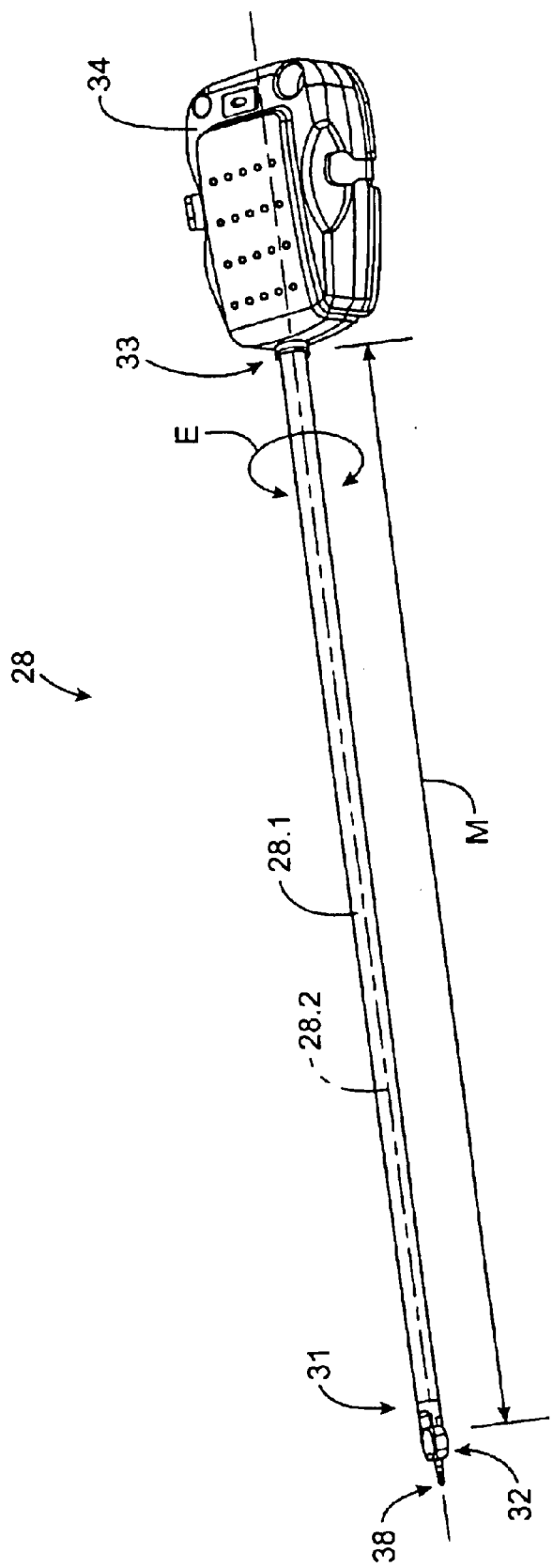
FIG. 2 is a perspective illustration of a robotic surgical tool which may be used with a robotic surgical system as in FIG. 1.

Referring now to FIG. 2, surgical instrument 28 suitably includes an elongate shaft 28.1 having a proximal end 33 and a distal end 31, a pivot 32 and end effector 38 disposed at the distal end, and an instrument base 34 disposed at the proximal end. Base 34 is generally configured to releasably engage a robotic surgical system, such as robotic surgical system 10 in FIG. 1. In general, instrument 28 is engaged with system via base 34 (base not shown in FIG. 1) such that instrument 28 is releasably mountable on a carriage 37 which can be driven to translate along a linear guide formation 38 of the arm 26 in the direction of arrows P.

Figure 3:
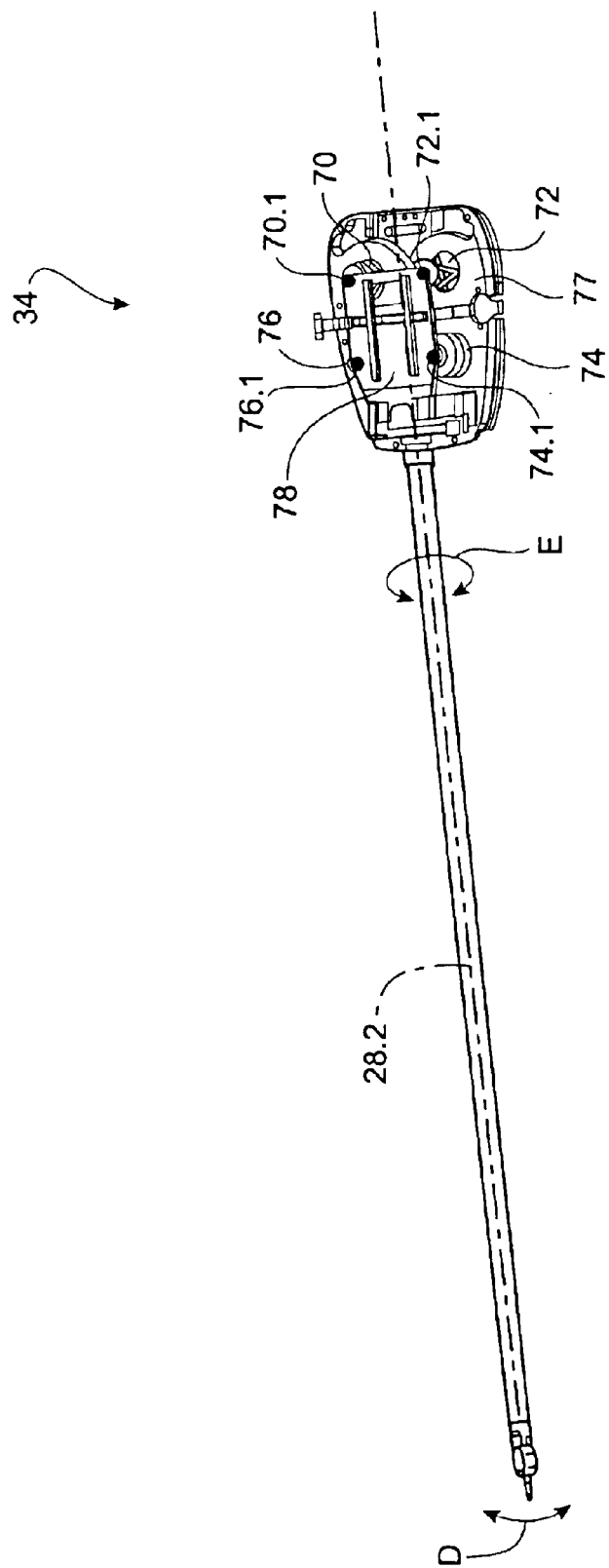
FIG. 3 is a perspective illustration of the robotic surgical tool in FIG. 2, with a cover of a tool base removed to show internal structures of the tool base.

With reference to FIGS. 2 and 3, shaft 28.1 is rotatably mounted on base 34 for rotation about an axis 28.2 extending longitudinally along the shaft 28.1 as indicated by the arrows E. Thus, when mounted on an arm assembly 26, end effector 38 may have a plurality of degrees of freedom of movement relative to manipulator arm 26, in addition to actuation movement of the end effector itself. The instrument may be translated along an insertion axis (Arrows P in FIG. 1). Typically, the instrument degrees of freedom include rotation about the axis 28.2 as indicated by arrows E, and in the case of instruments 28 including pivots 32, angular displacement as a whole about pivot 32 as indicated by arrows D. Alternatively, the distal pivoting degree of freedom may be omitted. A single pivot wrist, a multi-pivot wrist, a distal roll joint mechanism or other joints may be included to provide additional operational degrees of freedom to the end effector. Movement of end effector 38 relative to manipulator arm 26 controlled by appropriately positioned actuators, such as electric motors, or the like, which respond to inputs from an associated master control at the control station 12, so as to drive the end effector 38 to a required orientation as dictated by movement of the associated master control.

Referring now to FIG. 3, base 34 of surgical instrument 28 suitably includes transmission members 70, 72, 74, and 76, which include spools secured on shafts 70.1, 72.1, 74.1, and 76.1. Ends of shafts 70.1, 72.1, 74.1, 76.1 generally extend from a side 77 of base 34 to a mounting plate 78 within base 34 and are configured to rotate. Generally, the ends of shafts 70.1, 72.1, 74.1, 76.1 at side 77 of base 34 extend through side 77, to an outer surface of side 77 (not shown). At the outer surface, each shaft 70.1, 72.1, 74.1, 76.1 includes an engaging member (not shown) configured to releasably couple with a complementary engaging member (not shown) rotatably mounted on the carriage 37 of a robotic arm assembly 26 (see FIG. 1). The engaging members on carriage 37 are generally coupled to actuators (not shown), such as electric motors or the like, to cause selective angular displacement of each engaging member on the carriage 37 in response to actuation of its associated actuator. Thus, selective actuation of the actuators is transmitted through the engaging members on the carriage 37, to the engaging members on the opposed ends of the shafts 70.1, 72.1, 74.1, 76.1 to cause selective angular displacement of the spools 70, 72, 74, 76. Where more or fewer degrees of freedom are desired, the number of spools may be decreased or increased.

Figure 4:
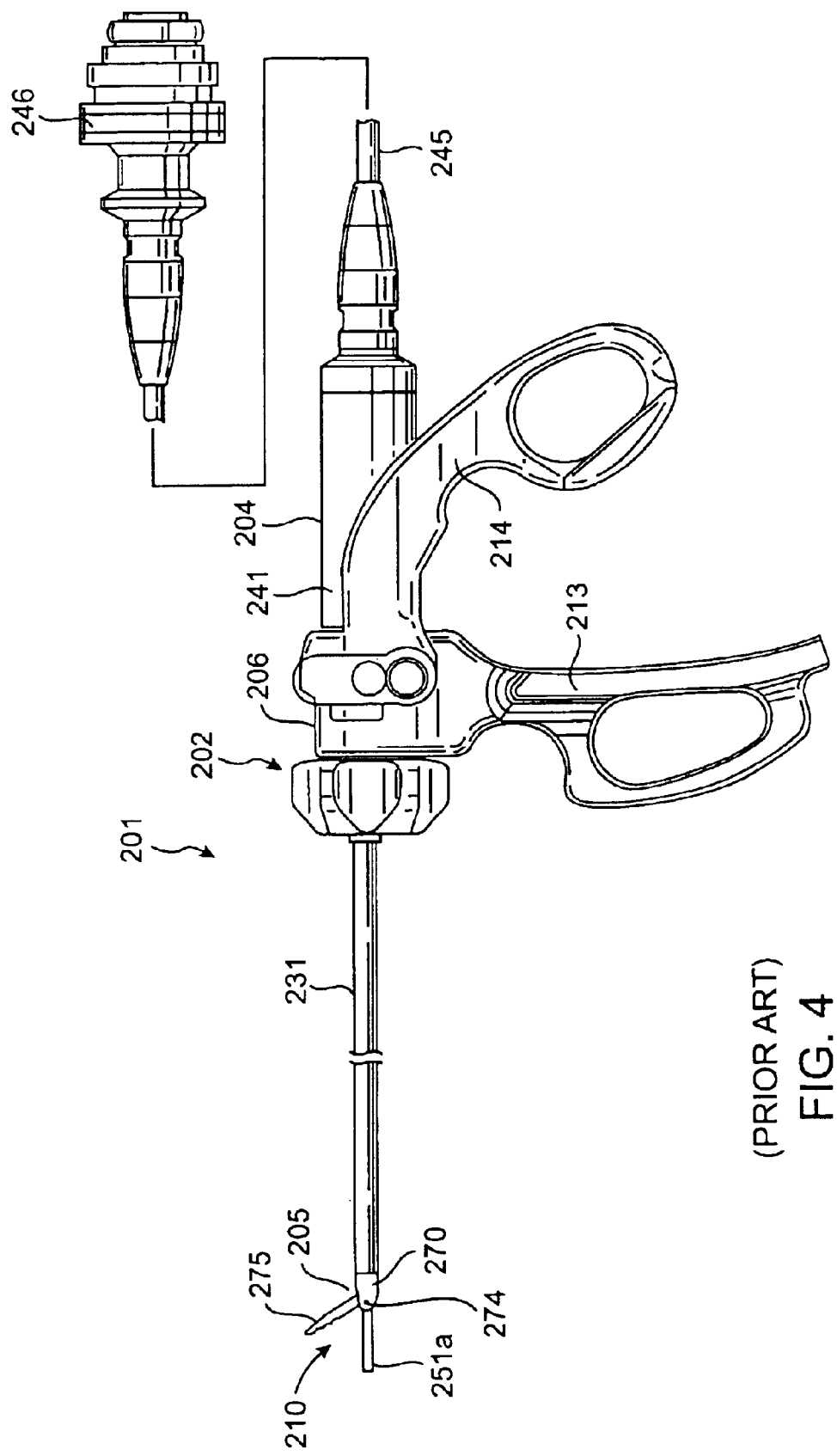
FIG. 4 is a side-view illustration of a manually operated ultrasound treatment apparatus as described in U.S. Pat. No. 6,193,709.
Figure 5:
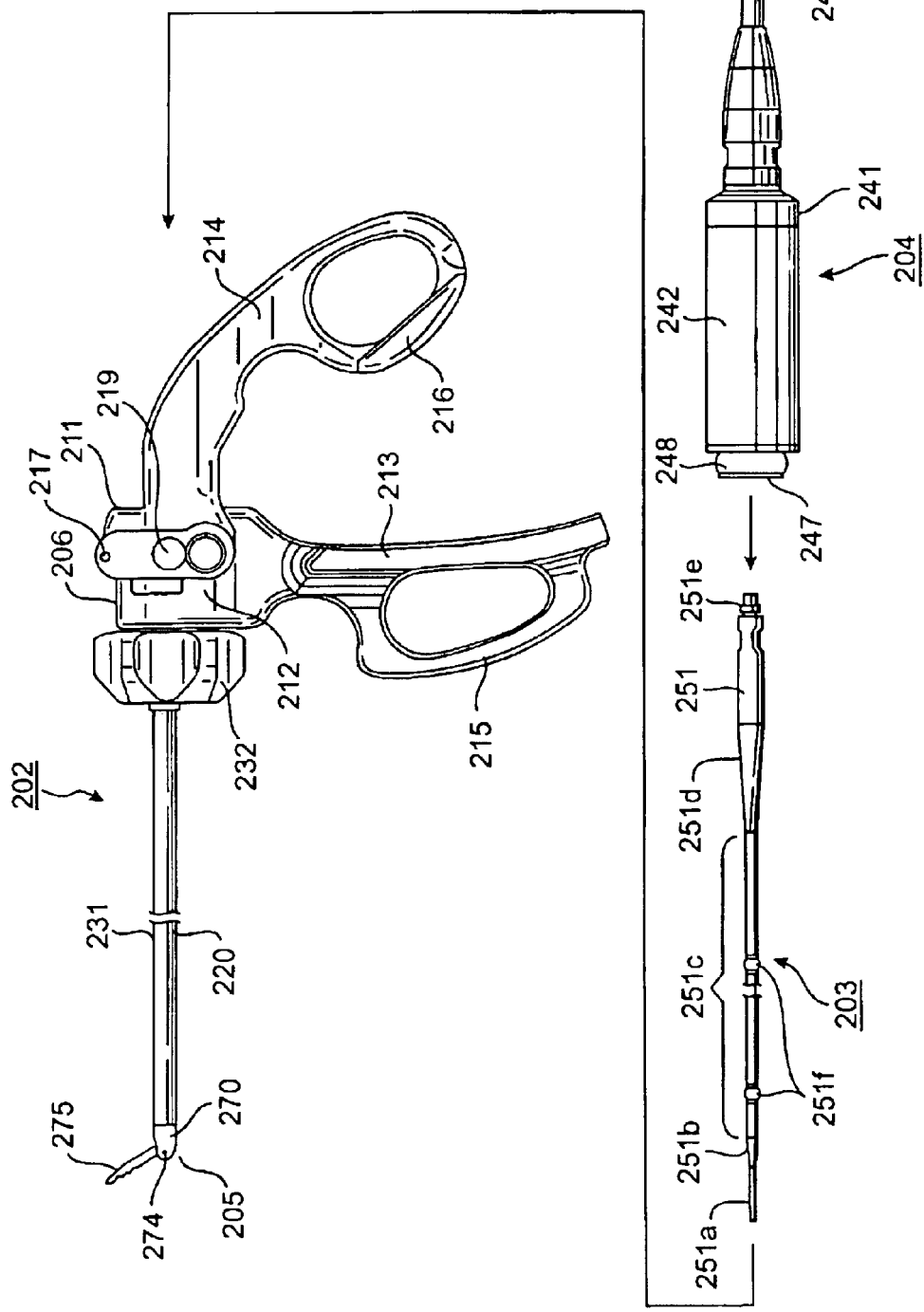
FIG. 5 is a side-view illustration of a manually operated ultrasound treatment apparatus as in FIG. 4, with a portion of the operative end of the apparatus shown in exploded view.

Referring now to FIGS. 4 and 5 an ultrasound treatment system 201 for manually-performed endoscopic surgery, as described in U.S. Pat. No. 6,193,709 (previously incorporated by reference), suitably includes a handle unit 202, a probe unit 203, and a vibrator unit 204. The following description of FIGS. 4–9 corresponds generally to the description of FIGS. 12–23 in U.S. Pat. No. 6,193,709.

Figure 9:
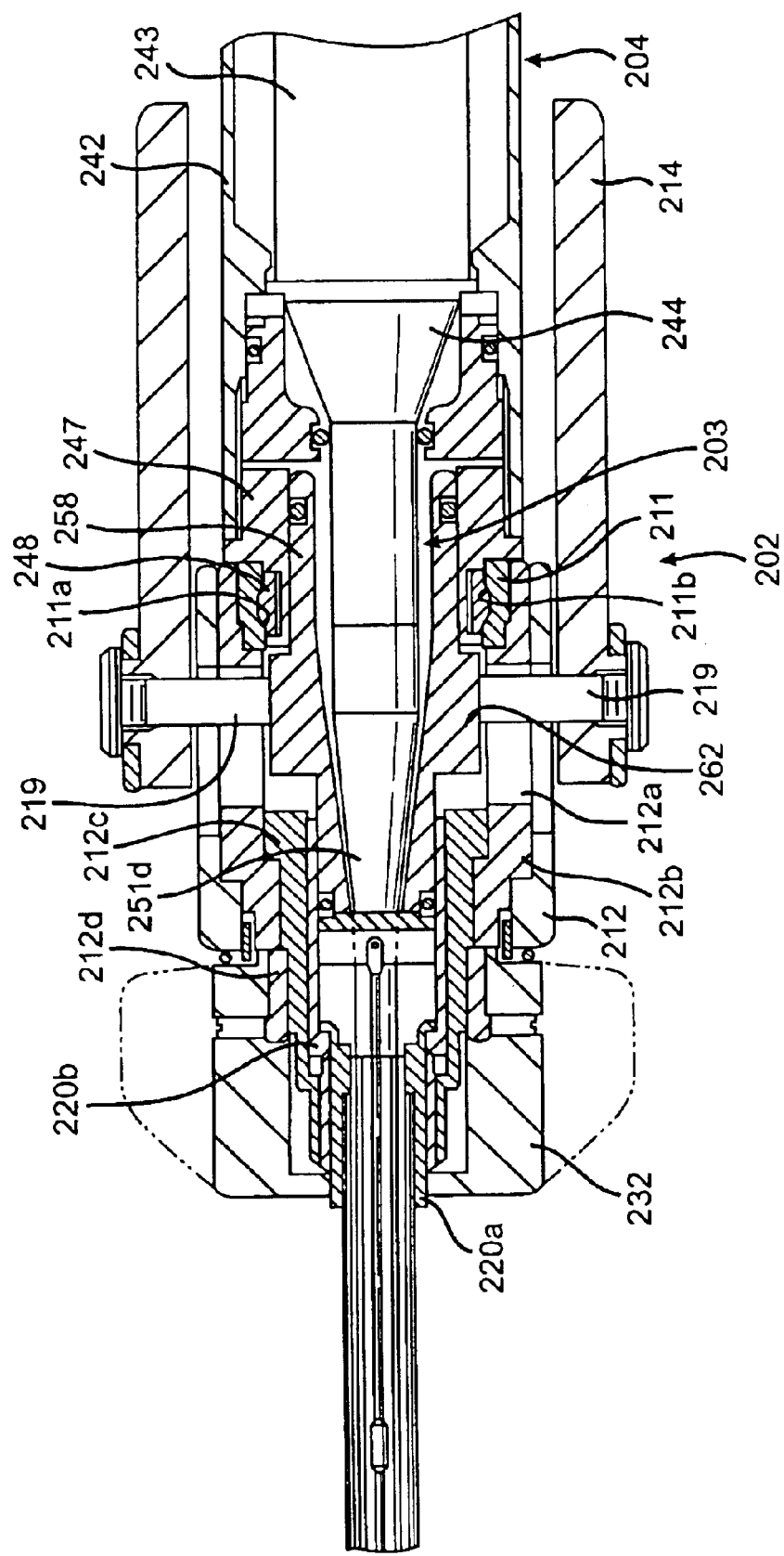
FIG. 9 is a cross-sectional side-view illustration of a portion of a manually operated ultrasound treatment apparatus as in FIGS. 4 and 5.

As shown in FIGS. 5 and 9, the vibrator unit 204 is formed as a hand piece 241. The hand piece 241 includes a cylindrical cover 242 that forms a grasping section. An ultrasonic transducer 243 and a horn 244 are arranged inside the cover 242. A hand piece cord 245 extends from the proximal end of the vibrator unit 204, and a hand piece plug 246 is provided on an end portion of the cord 245 (see FIG. 4). The plug 246 is connected electrically to an ultrasonic oscillator (not shown). The vibrator unit 243 is vibrated as it is supplied with electric power from the ultrasonic oscillator.

The horn 244, which is coupled to the ultrasonic transducer 243, amplifies ultrasonic vibration generated by the ultrasonic transducer 243 and enlarges its amplitude to a first phase. The distal end of the horn 244 is formed having an internal-thread portion to which the probe unit 203 is attached.

A connecting member 247 is attached to the distal end of the cover 242. The member 247 connects the vibrator unit 204, along with the probe unit 203 combined therewith, to the handle unit 202. More specifically, the connecting member 247 is provided with an engaging ring (C-shaped ring) 248 having a semicircular profile. The vibrator unit 204 is connected to the handle unit 202 as the ring 248 is caused elastically to engage an engaging groove 211a of a vibrator connecting section 211 (mentioned later) of the unit 202.

As shown in FIG. 5, the probe unit 203 is formed as a rod-shaped vibration transmitting member 251 for transmitting the ultrasonic vibration generated by the ultrasonic transducer 243. An external-thread portion 251e to be screwed into the internal-thread portion at the distal end of the horn 244 of the vibrator unit 204 is formed on the proximal end of the transmitting member 251. The transmitting member 251 includes a proximal-side horn 251d, intermediate portion 251c, distal-side horn 251b, and columnar distal end portion 251a. The proximal-side horn 251d further enlarges the amplitude of the ultrasonic vibration, amplified by the horn 244, to a second phase. The intermediate portion 251c is situated on the distal end side of the horn 251d. The distal-side horn 251b, which is situated on the distal end side of the intermediate portion 251c, enlarges the amplitude of the ultrasonic vibration, amplified by the horn 251d, to a final phase. The distal end portion 251a is situated on the distal end side of the horn 251b (or on the distal end side of the vibration transmitting member 251).

The ultrasonic vibration from the probe ultrasonic transducer 243, amplified by the horns 244, 251d and 251b, is transmitted to the distal end portion 251a, whereupon the end portion 251a vibrates. Further, the distal end portion 251a, along with a distal acting section 205 (mentioned later) of the handle unit 202, constitutes a treatment section 210 of the ultrasonic treatment apparatus 201.

As shown in FIG. 5, the handle unit 202 includes an operating section 206, the insertable sheath section 231 formed of a long sheathing tube 220 that is rotatably attached to the operating section 206, and the distal acting section 205 on the distal end of the insertable sheath section 231.

The operating section 206 includes an operating section body 212, a fixed handle 213 formed integrally with the body 212, and a movable handle 214. The operating section body 212 is provided with the vibrator connecting section 211 on its proximal end. The vibrator unit 204 is removably connected to the connecting section 211. The movable handle 214 is rockably mounted on the operating section body 212 (fixed handle 213) by means of a handle pivot 217. In this case, the handle pivot 217 is situated on the opposite side of the longitudinal central axis of the insertable sheath section 231 from the fixed handle 213. Thus, the movable handle 214 is rocked around a fulcrum that is situated above the longitudinal central axis of the sheath section 231. Further, the handle 214 has engaging pins 219 on or near the central axis of the sheath section 231. The pins 219 can engage a transmitting member 258 (see FIG. 8, mentioned later) in the operating body 212.

Figure 8:
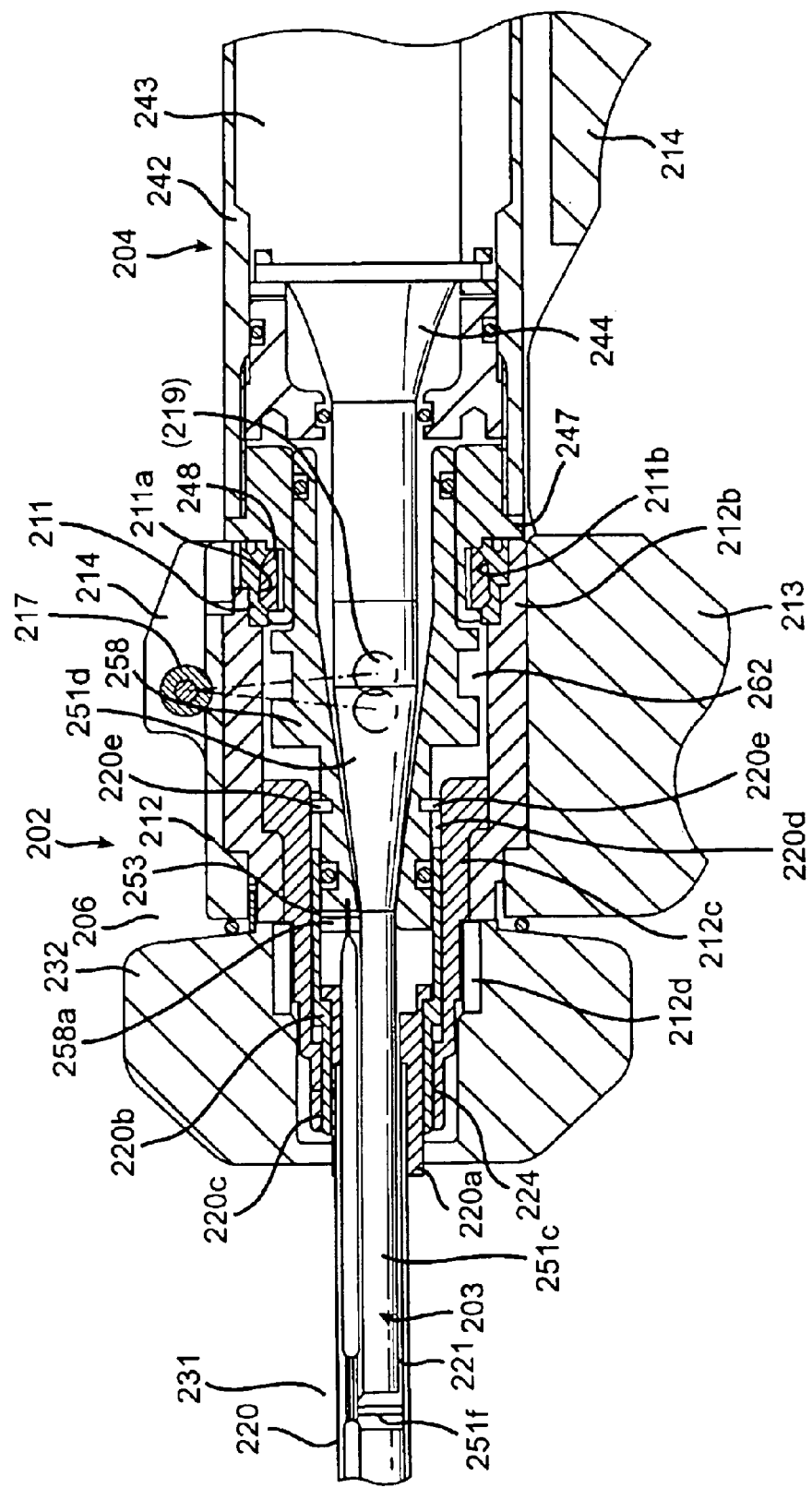
FIG. 8 is a cross-sectional side-view illustration of a portion of a manually operated ultrasound treatment apparatus as in FIGS. 4 and 5.

As shown in detail in FIGS. 8 and 9, a cylindrical interpolative member 212b is inserted and fastened in the operating section body 212. In this case, the distal end portion of the member 212b is held between a nut 212d, which is fitted in the distal end portion of the operating section body 212, and a cylindrical rotating member 212c, which is inserted and fastened in the distal end portion of the member 212b. Further, the cylindrical transmitting member (rotor) 258 is disposed inside the interpolative member 212b. The vibration transmitting member 251 is passed through a bore of the member 258. In an assembled state, the proximal-side horn 251d of the transmitting member 251 and the proximal-side portion thereof are arranged in the bore of the transmitting member 258. Moreover, an engaging groove 262 is formed on the outer peripheral surface of the transmitting member 258. Fitted in the groove 262 are the engaging pins 219 of the movable handle 214, which individually penetrate through-holes 212a in the operating section body 212 and the interpolative member 212b.

The annular vibrator connecting section 211 is attached to the inner peripheral surface of the proximal end portion of the interpolative member 212b by screwing and/or an adhesive such as glue. The engaging groove 211a is formed on the inner peripheral surface of the connecting section 211. The groove 211 has a conical engaging surface 211b on its proximal end side. The engaging surface 211b is designed to fit the curved outer peripheral surface of the engaging ring 248 that is attached to the connecting member 247 of the vibrator unit 204.

A cylindrical rotary knob 232 is attached to the nut 212d by means of a V-groove on the nut 212d and a cone-point setscrew. The proximal end portion of the sheathing tube 220 of the insertable sheath section 231 is inserted in a bore of the knob 232. An end member 220 a is fitted on the outer periphery of the proximal end portion of the tube 220 in the bore of the knob 232. The distal end portion of a connecting cylinder 220b is fitted and fixed on the outer periphery of the end member 220a by adhesive bonding. A thread portion 224 is formed on the outer peripheral surface of the distal end portion of the cylinder 220b. The distal end portion of the rotating member 212c, which extends in the bore of the rotary knob 232, is screwed on the thread portion 224. Further, the proximal end side of the connecting cylinder 220b is inserted into a bore of the rotating member 212c, and is held between the member 212c and the distal end portion of the transmitting member 258 in a manner such that it can move back and forth. The position (or longitudinal movement) of the cylinder 220b in the member 212c can be adjusted by rotating a nut 220c, which is screwed on the thread portion 224 of the cylinder 220b and engages the distal end of the member 212c. The connecting cylinder 220b has an engaging groove 220d on its proximal end. As a positioning pin 220e that protrudes from the transmitting member 258 engages the engaging groove 220d, the cylinder 220b is restrained from rotating relatively to the member 258.

As shown in FIGS. 4 and 5, the distal acting section 205 includes a holding member 270, which is attached to the distal end portion of the sheathing tube 220, and an open-close member 275 of a single-swing type, which is rockably (pivotably) attached to the member 270 by means of pivots 274. The acting section 205, along with the distal end portion 251 a of the vibration transmitting member 251 of the probe unit 203, constitutes the treatment section 210 of the ultrasonic treatment apparatus 201.

The open-close member 275 can hold a living organism in cooperation with the distal end portion 251 a of the vibration transmitting member 251 so that the organism is pressed against the distal end portion 251 a that is undergoing the ultrasonic vibration. Thus, vibration energy can be transmitted from the distal end portion 251 a to the organism. The member 275 also functions as an exfoliating forceps for exfoliating living organisms.

As shown in FIGS. 6 and 7, the open-close member 275 is composed of a pair of opposite side walls 275a and 275b, a proximal-side connecting portion 275c connecting the respective proximal-side upper end portions of the side walls 275a and 275b, a distal-side connecting portion 275d connecting the respective distal end portions of the side walls 275a and 275b, and attachment portions 275e extending individually downward from the respective proximal end portions of the side walls 275a and 275b.

A slit 234 is defined between the side walls 275a and 275b, and a grasping member 282 is located in the slit 234 for rocking motion. The member 282 can grasp the living organism in cooperation with the vibration transmitting member 251. More specifically, the grasping member 282 is connected integrally to a jaw 278 by means of a cylindrical collar member 277a so that the jaw 278 is held between the members 282 and 277a. Further, an attachment portion 282a of the member 282, which is situated in the slit 234, is rockably attached to the open-close member 275 by means of a pivot pin 277. In this case, the collar member 277a penetrates the attachment portion 282a of the grasping member 282 in the slit 234 and the jaw 278, while the pin 277 is passed through the member 277a. The width of the slit 234 is made greater than that of the attachment portion 282a of the grasping member 282 that is fitted in the slit 234.

FIGS. 10–19 show a preferred embodiment of a robotic tool 80 having aspects of the present invention. The tool 80 includes an ultrasound treatment instrument assembly which may have a number of features which are generally similar to portions of the ultrasonic treatment instrument shown in FIGS. 5–9. As a matter of cost and convenience, portions of a suitable OEM ultrasound instrument (for example, the SonoSurg® ultrasonic treatment instrument model T3070 made by Olympus Optical Co., Ltd., of Tokyo, Japan) may be modified and included as a subassembly of the robotic tool 80. The above referenced U.S. Pat. No. 6,193,709 describes an ultrasound treatment instrument generally similar to the SonoSurg® instrument. Likewise, portions of the generally similar Ultracision® Harmonic Scalpel® LaparoSonic® Coagulating Shears, now made by Ethicon Endo-Surgery, Inc, of Cincinnati, Ohio., may be included as subassemblies of the robotic tool 80. A description of an ultrasound treatment instrument generally similar to the LaparoSonic® Coagulating Shears is included in U.S. Pat. No. 5,322,055, which patent is hereby incorporated by reference. The tool 80 may be used in operative association with a suitable prior art OEM ultrasound driver transducer, power supply and control system (for example, the SonoSurg® model T2H made by Olympus Optical Co., Ltd., of Tokyo, Japan) to provide ultrasound energy supply and control functions.

Figure 10:
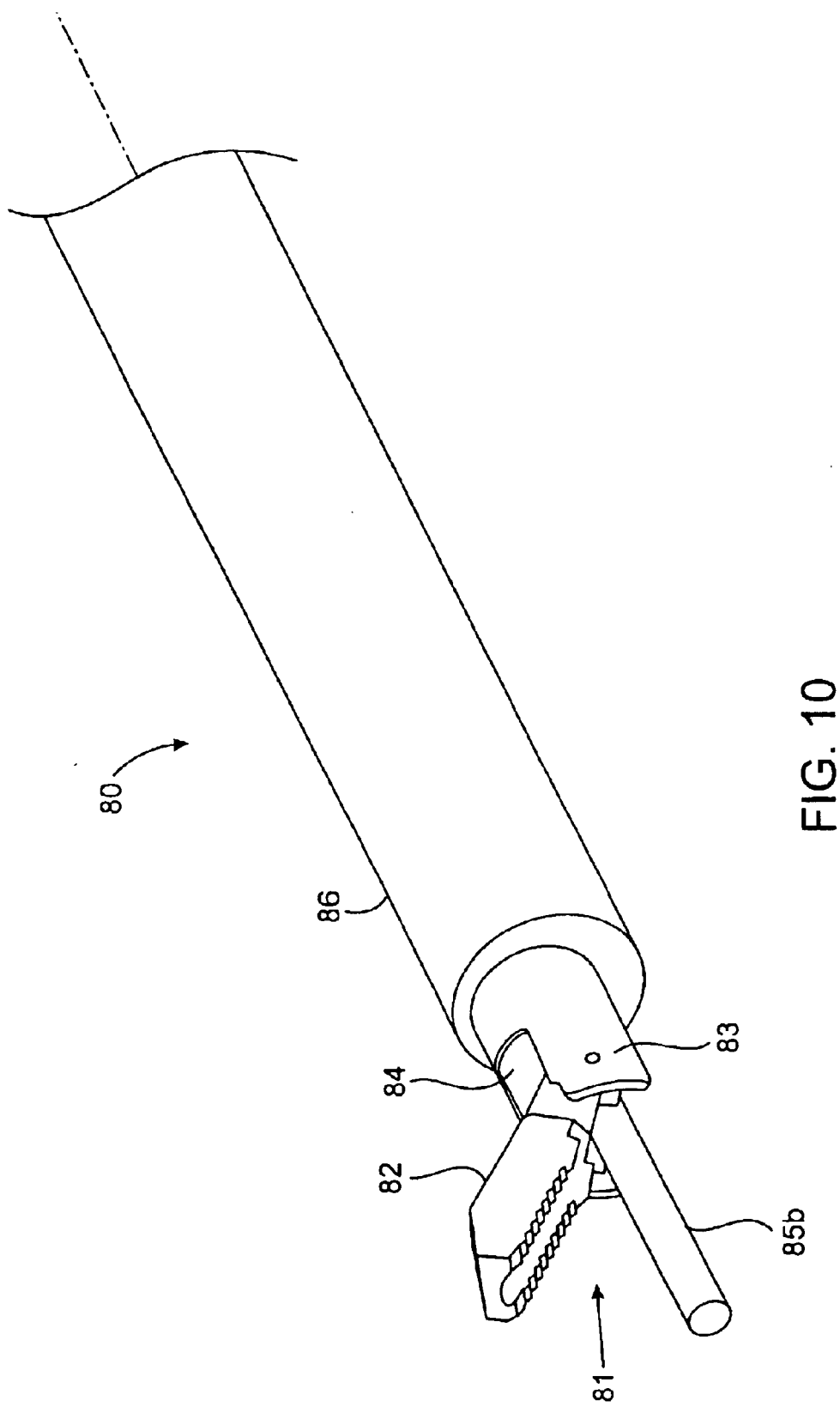
FIG. 10 is a perspective illustration of a distal portion of a robotic surgical tool according to an embodiment of the present invention.
Figure 13:
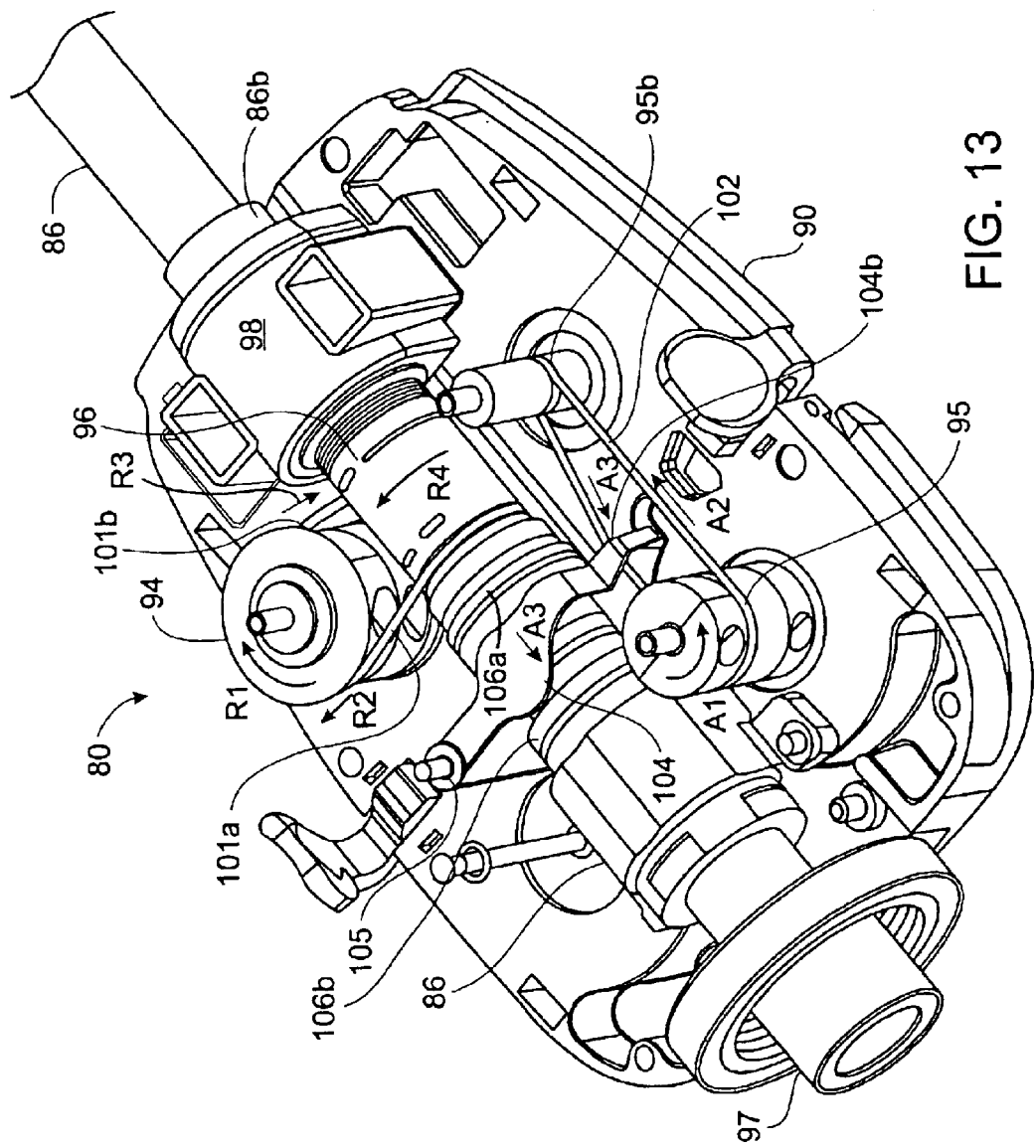
FIG. 13 is an enlarged perspective illustration of a tool base as shown in FIG. 12c.
Figure 16B:
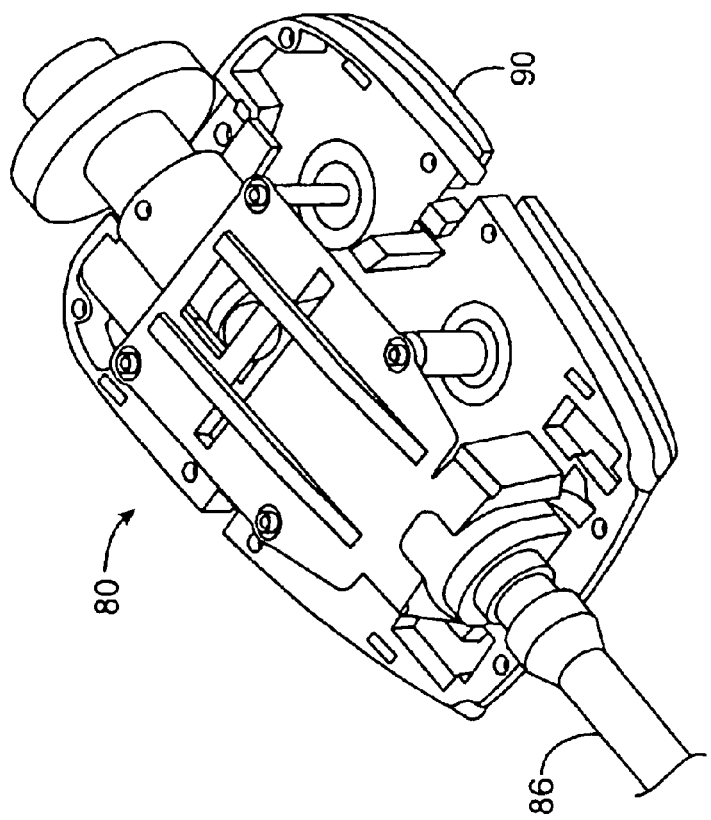
FIGS. 16a–d are perspective illustrations of a tool base according to an embodiment of the present invention, in progressive stages of disassembly.
Figure 16A:
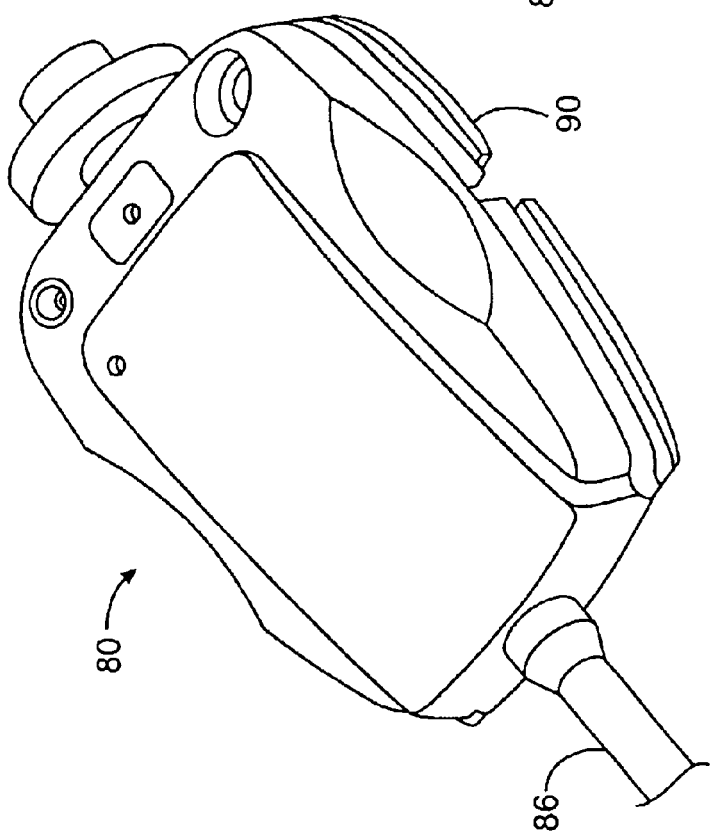
Figure 16D:
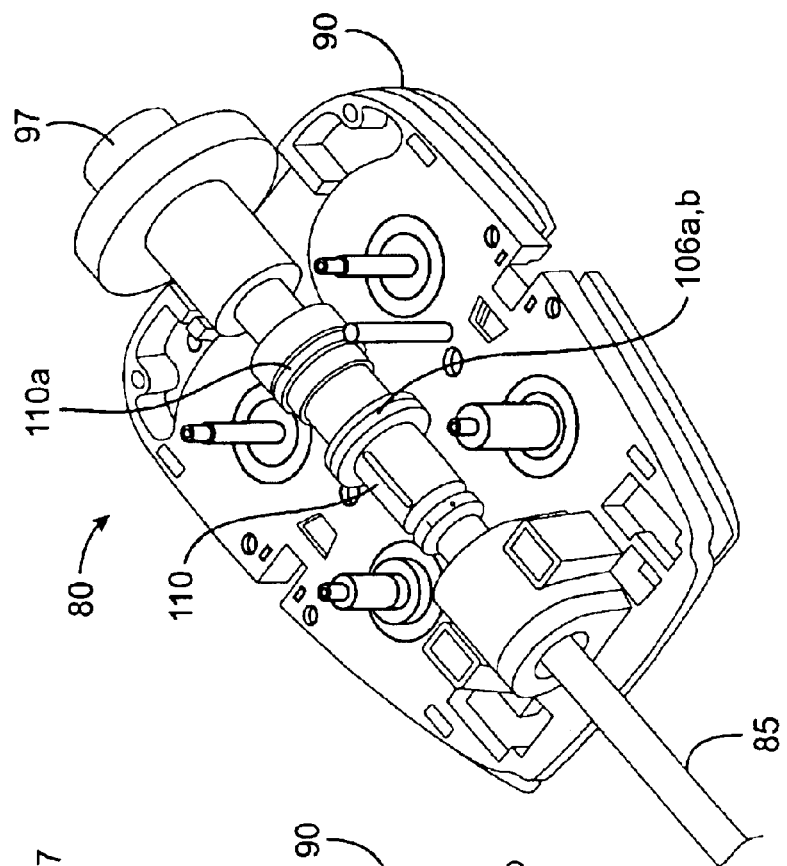
Figure 16C:
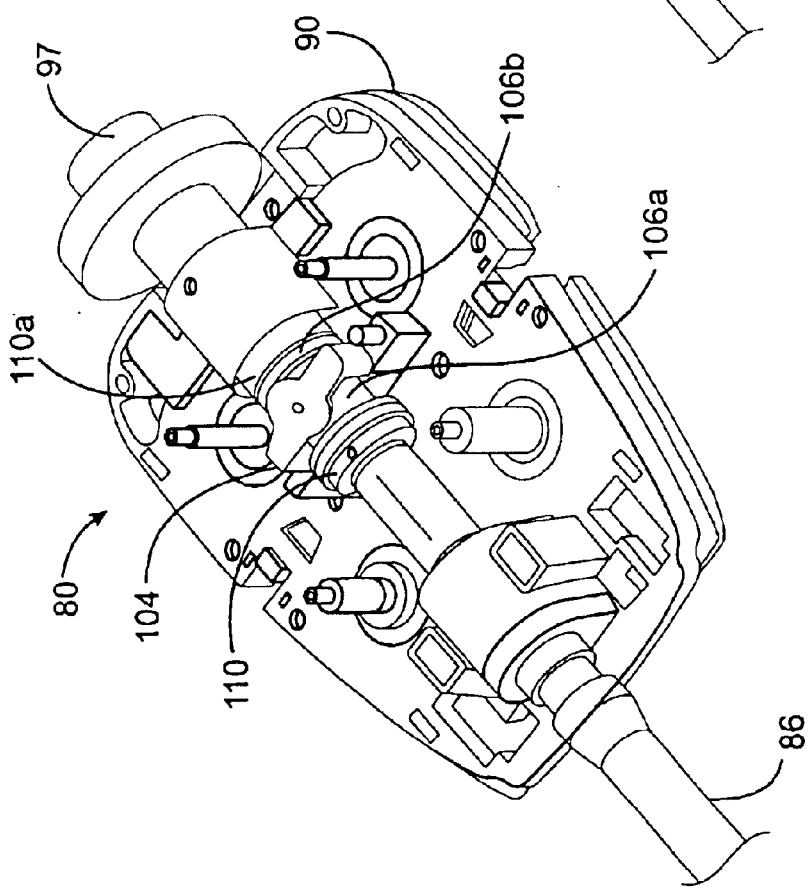

Referring now to FIGS. 10 and 11c, a distal portion of a robotic surgical instrument 80 according to various embodiments of the present invention suitably includes a shaft 84, covered by a sheath 86, with an end effector 81 at the distal end of shaft 84. End effector 81 includes a gripper 82 hingedly attached to shaft 84 at a hinge 83, and an ultrasonic probe tip 85b. In one embodiment, the distal portion of surgical instrument 80 also includes a distal sealing ring 87 (FIG. 11c).

Generally, ultrasound probe tip 85b is configured to delivery ultrasound energy at a surgical site for cutting, cauterization or any other suitable purpose. As such, ultrasound probe may be designed to have any suitable configuration. For example, ultrasound probe tip 85b may comprise a cylindrical probe with a rounded tip, as in FIG. 10, or may alternatively comprise a triangle-shaped probe, a square probe, a probe with a flat or pointed tip, a shorter probe, a longer probe or the like.

According to an aspect of the present invention, gripper 82 is configured to be movable at hinge 83 such that the distal end of gripper 82 may be moved toward ultrasound probe tip 85, 85b to grip tissue or other substances between gripper 82 and probe tip 85b, and may be moved away from probe tip 85b to release tissue. For example, gripper 82 may be used to grip tissue and position it in contact with ultrasound probe tip 85b to enable cutting or cauterization by probe tip 85b. As such, gripper 82 may have any suitable configuration for holding, gripping or otherwise moving tissue against probe tip 85b. For example, gripper 82 may include teeth, as in FIG. 10, or may have straight, flat edges, or one tooth or other gripping mechanism or the like.

According to another aspect of the invention, one or more axes for freedom of motion of end effector 81 may be included in the distal portion. For example, in one embodiment, shaft 84 is configured to rotate with sheath 86, enabling end effector 81 to rotate about the long axis of the surgical instrument. In another embodiment, a wrist-like mechanism at the connection of shaft 84 to end effector 81 allows hinge-like movement of end effector 81 in relation to shaft 84. In another embodiment, as already described, hinge 83 allows movement of gripper 82. Any suitable combination of such hinges, wrist-like mechanisms, rotational devices and the like are contemplated within the scope of the present invention.

Referring now to FIGS. 11a and 11b, a base 90 of surgical instrument 80 according to various aspects of the present invention includes multiple components, such as actuator pulleys, idler pulleys, actuator rods and the like. Embodiments of such components are described in more detail below, but generally, the components of base 90 are configured to enable coupling of surgical instrument 80 with a robotic surgical system. More specifically, components of base 90 enable forces originating at one or more master controllers of a robotic surgical system to be transmitted to end effector 81 to achieve an effect at a surgical site. Some of the components of various embodiments of base 90 and surgical instrument 80 are generally similar to those described in U.S. application Ser. No. 09/398,958, filed Sep. 17, 1999, and U.S. application Ser. No. 09/418,726, filed Dec. 6, 1999 (both previously incorporated herein by reference).

Referring now to FIGS. 12a–12c base 90 is shown with an enclosing cover 91 in place (FIG. 12a), with enclosing cover 91 removed to show an upper chassis 93 (FIG. 12b) and with upper chassis 93 removed (FIG. 12c). Upper chassis 93 is generally configured to rotatably hold and support one end of one or more actuator spools 94, 95 and one or more idler spools 95a. Base also suitably includes a rear connector 97 for coupling base 90 to an ultrasound driver (not shown).

FIG. 12d is a perspective illustration of a surgical instrument 80, showing base 90 with covering 91, sheath 86 enclosing shaft, and end effector 81.

Referring now to FIGS. 13, 14a, 14b, 15a and 15b, various views of base 90 as shown in FIG. 12c are illustrated. In various embodiments, base 90 includes a shaft receiver 86b, a bearing housing 98, a roll drum 96, a actuator tube 110, a roll spool 94, an upper cable 101a, and a lower cable 101b. Shaft receiver 86b is generally configured to attach roll drum 96 to shaft/sheath 86. Roll drum 96 is in turn rotatably supported by bearings within bearing housing 98. Roll drum 96 interconnects to receiver 86b and surrounds actuator tube 110. Roll cable 101 spans between roll spool 94 and roll drum 96 as follows: upper cable 101a wraps around drum 96 at its rear portion (clockwise as seen from rear) and also wraps around spool 94 upper portion (clockwise as seen from above). In the opposite sense, lower cable 101b wraps around the front portion of drum 96 and around the lower portion of spool 94. Thus, when spool 94 is rotated by an interface member of a robotic surgical system, as shown by Arrow R1, roll cable 101 transfers rotational motion to drum 96 by corresponding winding and unwinding of roll cable 101 around spool 94 and drum 96. For example, as spool 94 is rotated as shown by Arrow R1, upper cable 101a moves as shown by Arrow R2 and lower cable 101b moves as shown by Arrow R3, causing drum 96 and shaft 86 to rotate as shown by Arrow R4. The motion is reversible and controllable by the robotic surgical system.

According to one aspect of the present invention, gripper 82 of end effector 81 is movable by one or more actuator rods housed within shaft 86. The motive force for actuating the rod is supplied by actuator spool 95 which engages an interface member (not shown) on a robotic surgical system. A cable loop 102 wraps around spool 95 and also around idler spool 95b in a closed loop extending in a longitudinal direction generally parallel as spaced apart on the right side of shaft 86. The inner portion of loop 102 is fixed to the right end 104b of pivot bar or rod 104, the left hand end of bar 104 is pivoted at pivot pin 105 on the left hand side of shaft 86. The bar 104 (also referred to as a "square hole rod") extends above, below and across shaft 86, and contacts actuator assembly 110 at a medial portion of bar 104 above and below shaft 86.

Referring now to FIGS. 14a and 14b, various embodiments of base 90 suitably include additional components, including one or more: drive shafts 144 for coupling pulleys with a robotic surgical system; attachment pins and/or rings 140; holders and lock nuts 141; washers and bushings 106a,b to reduce friction; bushings for pins 142; tube and grip assemblies 148; pins 149 to align roll pulleys and actuators; retainers 147 to hold square hole rod washers and bushings in place; pins 146 to align and hold tube and grip assembly 148; retaining pins, rings and caps 145 to hold roll pulley and outer tube assembly; and rods 111 to connect actuator to grip.

Figure 17:
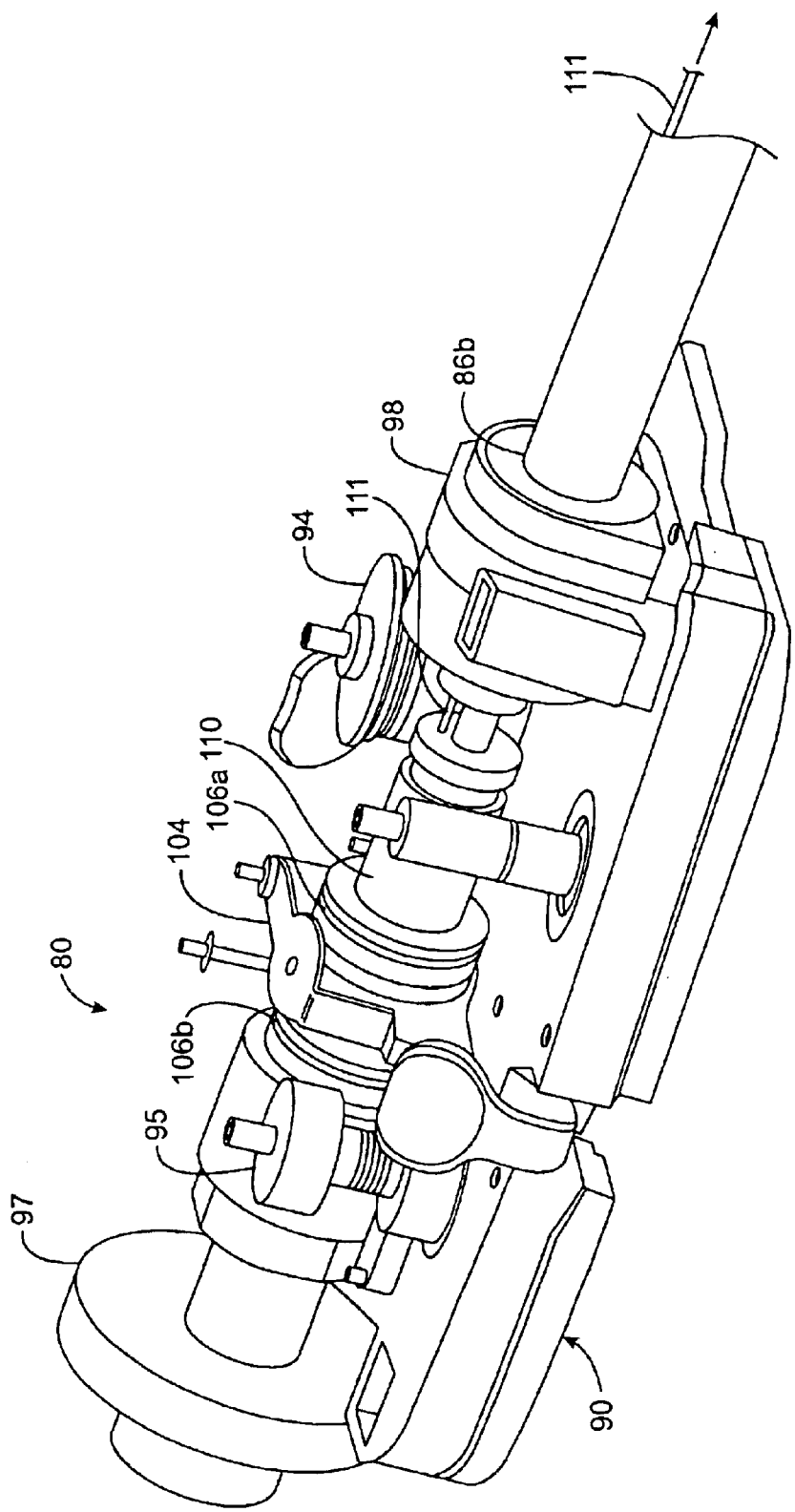
FIG. 17 is a perspective illustration of a portion of a tool base according to an embodiment of the present invention.
Figure 18:
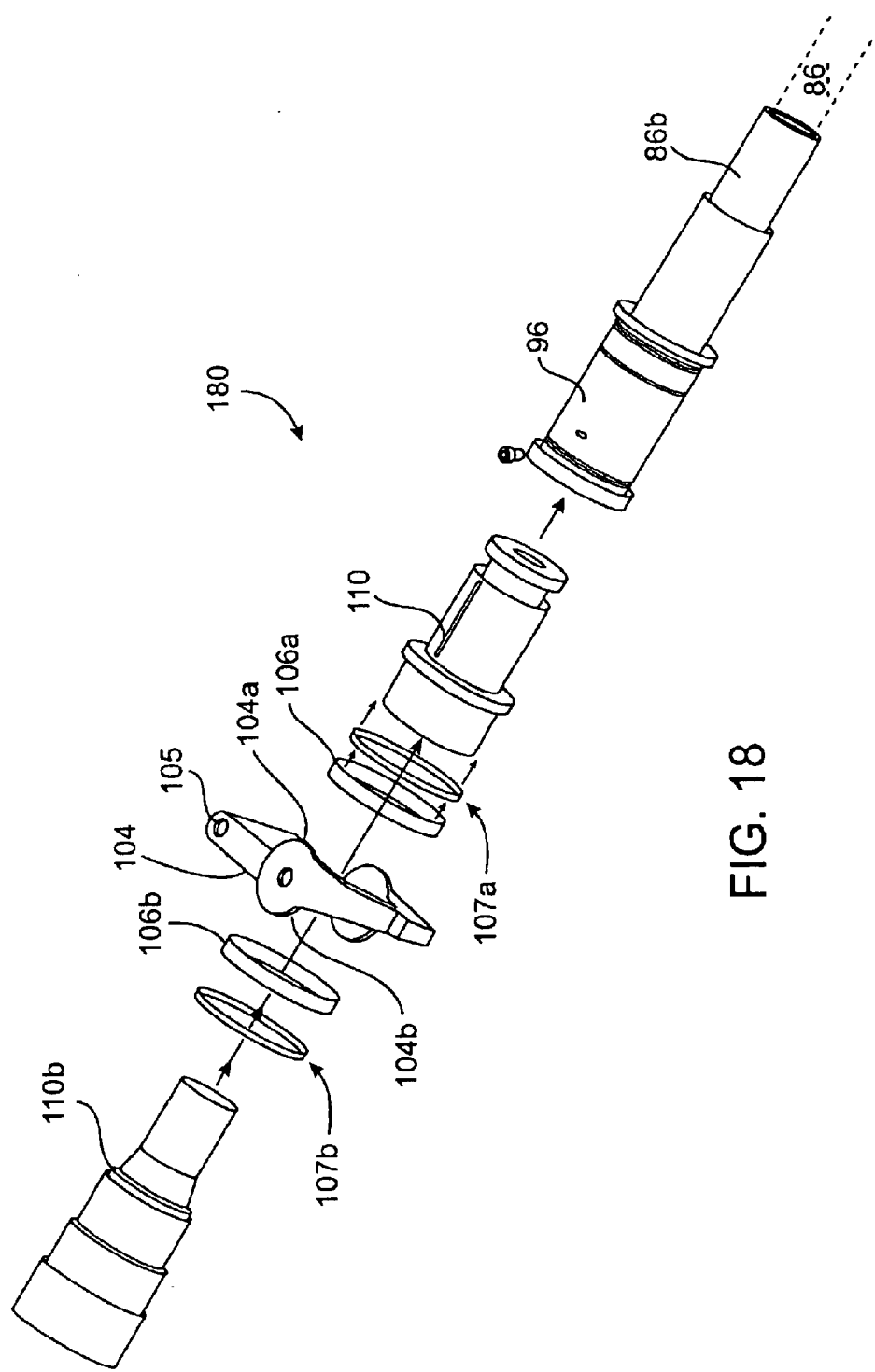
FIG. 18 is an exploded perspective illustration of a portion of a tool base according to an embodiment of the present invention.
Figure 19:
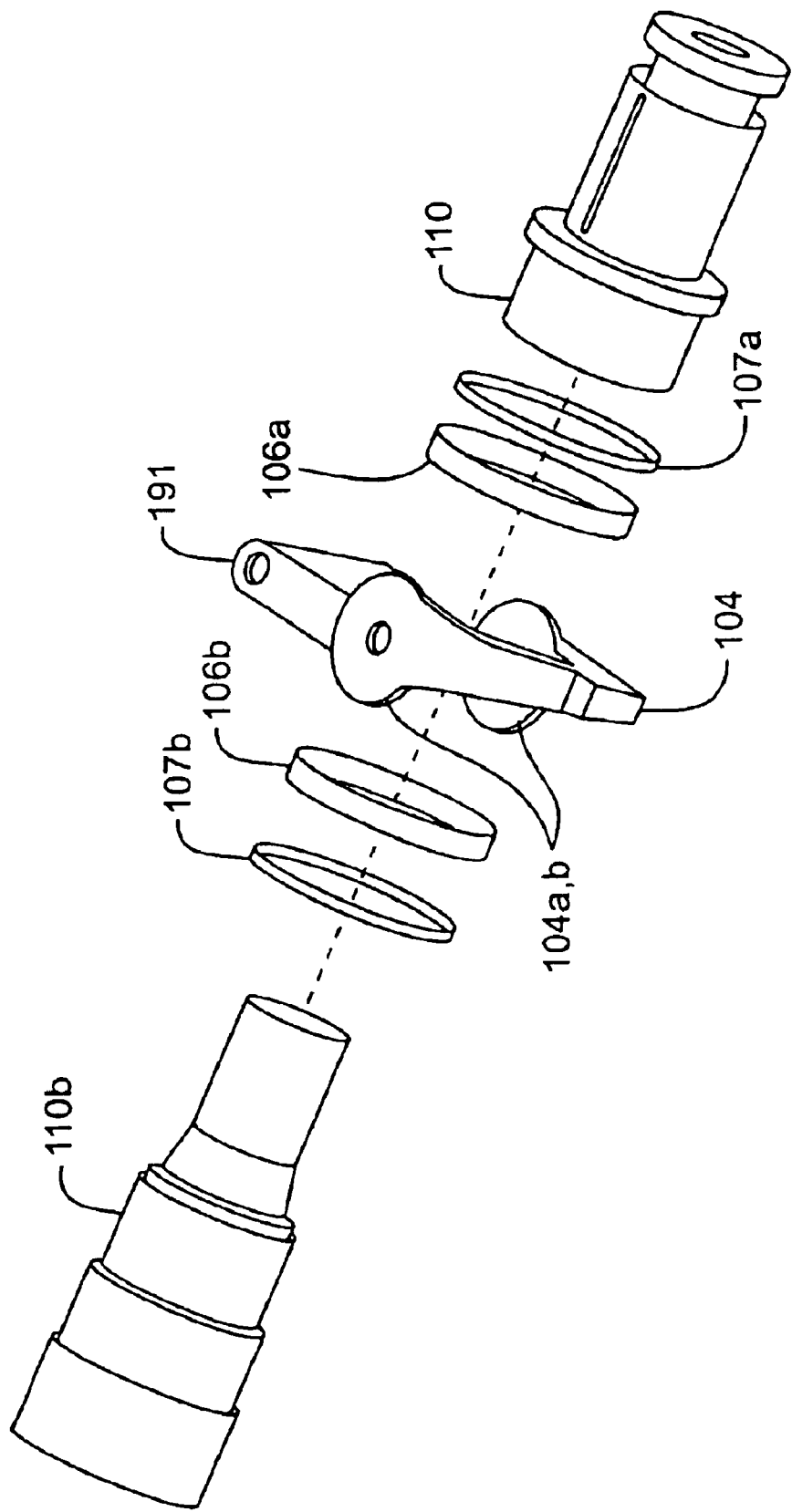
FIG. 19 is an exploded perspective illustration of a portion of a tool base according to an embodiment of the present invention.

Referring now to FIGS. 17–19, in one embodiment bar 104 is configured to extend under shaft/sheath 86 and loop around shaft/sheath 86, with sufficient clearance from the shaft 86 to enable it to pivot freely within a desired range of motion. As spool 95 rotates counter-clockwise as shown by Arrow A1 (FIG. 13), loop 102 moves counter-clockwise as shown by Arrow A2, so that the inner portion of the loop moves bar 104 pivotally rearwards (towards the rear or proximal end of base 90). The distal and proximal side surfaces 104a,b of bar 104 bear on distal and proximal bushings 106a,b which in turn contact the actuator 110 to cause it to move rearward, in turn moving the actuator rod 111 rearward so as to close the gripper 82. Typically, due to mechanical advantage of the system, actuator 110 moves rearward through about one half of the range of motion of loop 102.

As discussed further below with respect to FIGS. 17–19, bushings 106a,b bear on actuator tube or ring 110 which is moved rearward or forward by bar 104 (as shown). The actuator ring extends concentrically within drum 96 and transfers this motion to actuator rod 111 which extends within shaft 86 distally to pivotally connect to gripper 82. As shown in FIGS. 14, 15, actuator rod 111 acts about a lever arm of gripper 82 to alternately open gripper 82 (rearward rod movement) or close gripper 82 (forward rod movement). Bushings 106a,b slidably bear on bar 104 so as transmit longitudinal forces to the actuator tube 110 as the shaft 86 is rotated, thus permitting gripper actuation at any angle of shaft rotation. Generally, this actuator motion is reversible and controllable by the robotic system, producing a controllable forward or rearward actuator 110 and rod 111 motion and in turn controllably opening and closing gripper 82.

According to another aspect of the invention, rear connector 97 on base 90 is generally configured to connect to a transducer driver to permit ultrasound energy to be transmitted through probe core 85 housed within shaft 86. In other embodiments, base 90 may include an internal ultrasound source, such that surgical instrument 80 may contain its own source of ultrasound energy.

FIGS. 17–19 illustrate details of the longitudinal coupling from bar 104 (often referred to as "square hole rod" due to the open midsection of the particular embodiment shown) to actuator tube 110. The motion of the midsection of bar 104 is transferred via bushings 106a,b to tube 110, which is moved rearward or forward by bushings 106a,b. Actuator ring 110 extends distally (drum 96 is omitted in FIG. 17 for clarity) and transfers this longitudinal motion to actuator rod 111 which extends within shaft 86 distally to pivotally connect to gripper 82.

FIGS. 18 and 19 are exploded views of an actuator tube assembly 180 according to an embodiment of the present invention. In addition to components of actuator tube assembly 180 previously described above, the assembly 180 also suitably includes additional washers 107a,b to reduce friction in the assembly. According to one aspect of the invention, as shown in FIGS. 18 and 19, actuator tube 110 includes retainer tube 110b. In one embodiment, retainer tube 110b threads into tube 110 when assembled, so as to "sandwich" or trap bushings 106a,b between flange portions of rings 110, 110b and the side surfaces 104a,b of bar 104.

FIGS. 20 through 23 illustrate an alternative example of an instrument embodiment 300 including aspects of the invention.

It should be noted that much of the description above with respect to the robotic instrument embodiment 80 of FIGS. 10–19, including incorporated references, is also relevant with respect to instrument 300, since in many cases generally similar structures of each instrument serve equivalent functions.

For convenience and to minimize manufacturing costs, selected OEM components of commercially available instruments may optionally be included in the instrument 300 described herein. FIGS. 24–27 are sheets of reproductions of the FIGS. 26–36 of U.S. Pat. No. 6,280,407, issued Aug. 28, 2001 to Manna, et al., entitled "Ultrasonic Dissection And Coagulation System", and assigned to United States Surgical Corporation of Norwalk, Conn., the entire contents of which are hereby incorporated by reference. The patent describes, among other things, a hand-held ultrasonic treatment instrument example generally similar to the AutoSonix* Ultra Shears* made by United States Surgical Corporation of Norwalk, Conn.

The instruments described in U.S. Pat. No. 6,280,407 include, among other things, a transducer portion, an ultrasonic core (vibration coupler) portion, a shaft/distal end effector portion, and an ultrasonic power supply/controller suitable for employment as parts of the instrument embodiment of FIGS. 20–23. For simplicity, in the description below the relevant parts shown and described in U.S. Pat. No. 6,280,407 will be presumed to be included in the instrument example 300, although it will be clear to one of ordinary skill in the art how to make and configure the production details of equivalent dedicated parts.

For convenience, an excerpt of U.S. Pat. No. 6,280,407, from column 11, line 50, to column 14, line 55, is included below. This excerpt includes description of FIGS. 26–36 of that patent, reproduced and attached as FIGS. 26–36 herein.

FIG. 26 illustrates another alternate embodiment of the ultrasonic instrument, shown generally as 412. Ultrasonic instrument 412 includes housing 422 and elongated body portion 424 extending distally from housing 422. Housing 422 is preferably formed from molded housing half-sections 422a and 422b and includes a barrel portion 426 having a longitudinal axis aligned with the longitudinal axis of body portion 424 and a stationary handle portion 428 extending obliquely from barrel portion 426. Ultrasonic transducer 430 is supported within and extends from the proximal end of housing 422 and includes a proximal fluted portion 431 configured to engage an attachment device to facilitate attachment and removal of transducer 430 from instrument 412. Jaw assembly 432 is disposed adjacent the distal end of elongated body portion 424 and is actuated by moving movable handle 436 with respect to stationary handle portion 428. Movable handle 436 and stationary handle portion 428 include openings 438 and 440, respectively, to facilitate gripping and actuation of ultrasonic instrument 412. Elongated body portion 424 is supported within rotatable knob 434 and may be selectively rotated by rotating knob 434 with respect to housing 422 to change the orientation of jaw assembly 432.

FIG. 27 illustrates elongated body portion 424 with parts separated. Elongated body portion 424 includes an outer tube 442 which is preferably cylindrical and has a proximally located annular flange 444 dimensioned to engage rotatable knob 434. An elongated actuator tube 446, which is also preferably cylindrical, is configured to be slidably received within outer tube 442 and includes a proximally located annular flange 448 dimensioned to engage coupling member 498 which is supported within housing 422. Although not shown, it is contemplated that a portion of actuator tube 446 and a portion of outer tube 442 adjacent flange 444 flares outwardly to provide additional clearance for vibration coupler 450. Vibration coupler 450 is dimensioned to extend through elongated actuator tube 446 and includes an enlarged proximal end 452 having a bore (not shown) configured to operatively engage ultrasonic transducer 430. The distal end of actuator tube 446 includes a pair of resilient arms 453 having distally located openings 455. The openings 455 are dimensioned to receive protrusions 461 formed on an adaptor 457. Arms 453 are flexible outwardly and engage adaptor 457. Cutting jaw 458 is monolithically formed with vibration coupler 450. Alternately, cutting jaw 458 and vibration coupler 450 can be formed separately and fastened together using any known connector, e.g., screw threads, friction fit, etc. Although not shown, a plurality of sealing rings can be molded or otherwise attached to the nodal points along vibration coupler 450 to seal between vibration coupler 450 and actuator tube 446.

Referring also to FIGS. 28A–C, a clamp 460 is operably connected to adaptor 457. Clamp 460 preferably includes a pair of longitudinally extending rows of teeth 462 which are spaced from each other a distance which permits cutting jaw 458 to be positioned between the rows of teeth 462. Teeth 462 function to grip tissue when the jaw assembly 432 is in a closed position to prevent tissue from moving with respect to cutting jaw 458 during vibration of the cutting jaw.

Pivot members or pins 466 are formed at the proximal end of clamp 460 and are configured to be received within open ended slots 468 in the distal end of outer tube 442. Slots 468 are open on one side thereof to permit clamp 460 to be retained therein. A longitudinally extending guide slot 470 formed in adaptor 457 is dimensioned to slidably receive pivot pin 466 and permit relative movement between adaptor 457 and clamp 460. A pair of camming members 472 are also formed on clamp 462 and are positioned to be received in cam slots 474 formed in the adaptor in 457.

Cutting jaw 458 includes blade surface 459 which is flat and angled downwardly toward its distal end to define a fixed acute angle $\theta$ of from about 10 degrees to about 20 degrees with respect to the longitudinal axis of the elongated body portion 424 and to the axis of vibration. The angled blade surface provides for good visibility at the surgical site. Preferably, angle $\theta$ is about 12 degrees, but greater angles such as 20 to 30 degrees are also envisioned. Alternately, blade surface 459 may be other than flat, e.g., sharpened, rounded, etc.

Clamp 460 is movable relative to cutting jaw 458 from an open position in which tissue contact surface 464 of clamp 460 is spaced from blade surface 459 to a closed or clamped position in which tissue contact surface 464 is in juxtaposed closer alignment with blade surface 459. In the clamped position, note the positioning of tissue contact surface 464 with respect to blade surface 459. Actuation of clamp 460 from the open position to the clamped position will be described in detail below.

Figure 29:
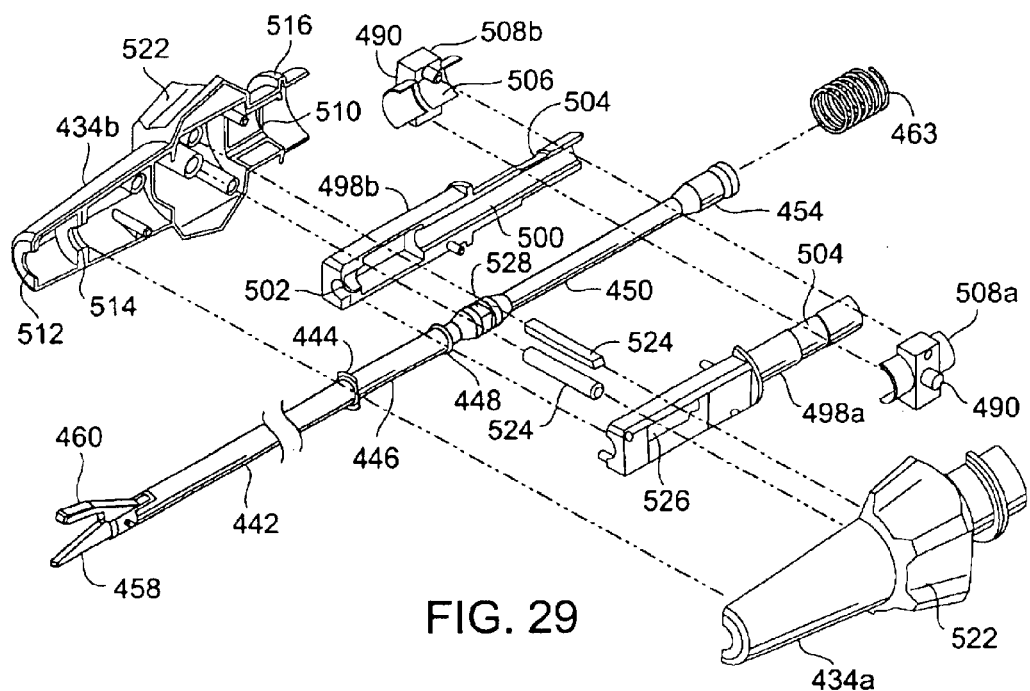
FIG. 29 is a side perspective view of the elongated body portion and rotation assembly of the ultrasonic instrument shown in FIG. 26.
Figure 30:
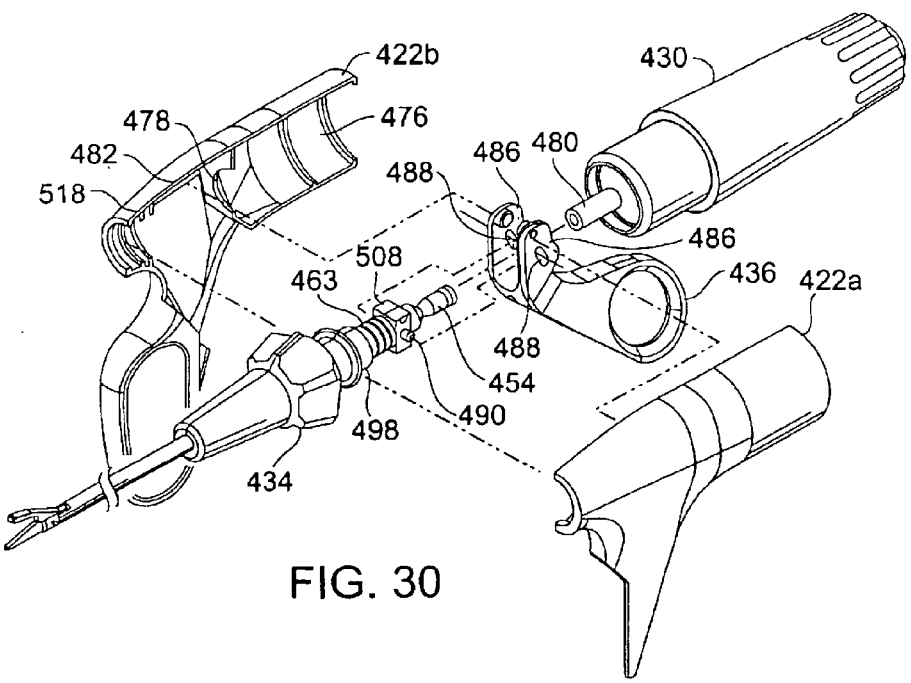
FIG. 30 is a side perspective view of the handle assembly and transducer assembly of the ultrasonic instrument shown in FIG. 26.

Referring to FIGS. 29 and 30, housing half-sections 422a and 422b define a chamber 476 configured to house a portion of ultrasonic transducer 430. Chamber 476 has an opening 478 communicating with the interior of housing 422. Ultrasonic transducer 430 includes a cylindrical stem 480 configured to be received in an opening in proximal end 454 of vibration coupler 450. In the assembled condition, proximal end 454 extends through opening 478 into engagement with cylindrical stem 480. Movable handle 436 is pivotally connected between housing half-sections 422a and 422b about pivot pin members 482 which are monolithically formed with housing half-sections 422a. A cam slot 488 formed in each leg 486 is configured to receive a protrusion 490 projecting outwardly from coupling member 498.

Coupling member 498 operatively connects movable handle 436 to actuator tube 446 and is preferably formed from molded half-sections 498a and 498b to define a throughbore 500 dimensioned to slidably receive the proximal end of vibration coupler 450.

Coupling member 498 has an inner distally located annular groove 502 dimensioned to receive annular flange 448 of actuator tube 446 and an outer proximally located annular groove 504 positioned to receive an annular projection 506 formed on the internal wall of swivel member 508. The projection 506 of swivel member 508 is movable through groove 504 to permit relative longitudinal movement between coupling member 498 and swivel member 508. A spring 463 is positioned between coupling member 498 and swivel member 508 to bias the swivel member 508 proximally with respect to coupling member 498. Swivel member 508 is preferably formed from molded half-sections 508a and 508b and permits rotation of coupling member 498 relative to movable handle 436. Protrusions 490 project outwardly from sidewalls of swivel member 508 and extend through cam slots 488 of movable handle 436.

Figure 31:
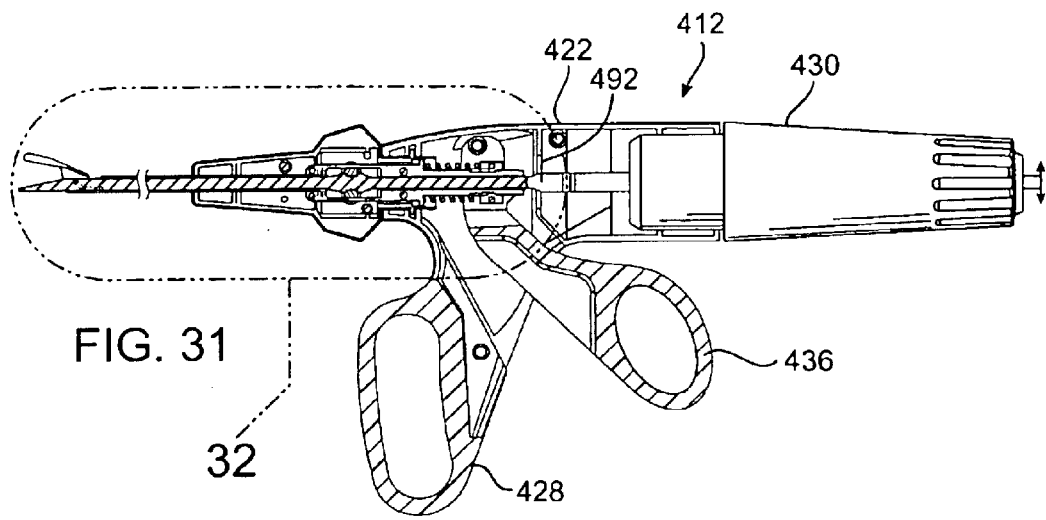
FIG. 31 is a side partial cross-sectional view of the ultrasonic instrument shown in FIG. 26 in the open position.
Figure 31A:
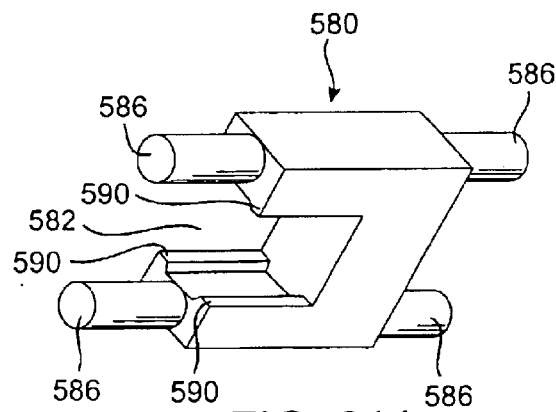
FIG. 31A is an enlarged perspective view of a C-clip locator for the vibration coupler.
Figure 32:
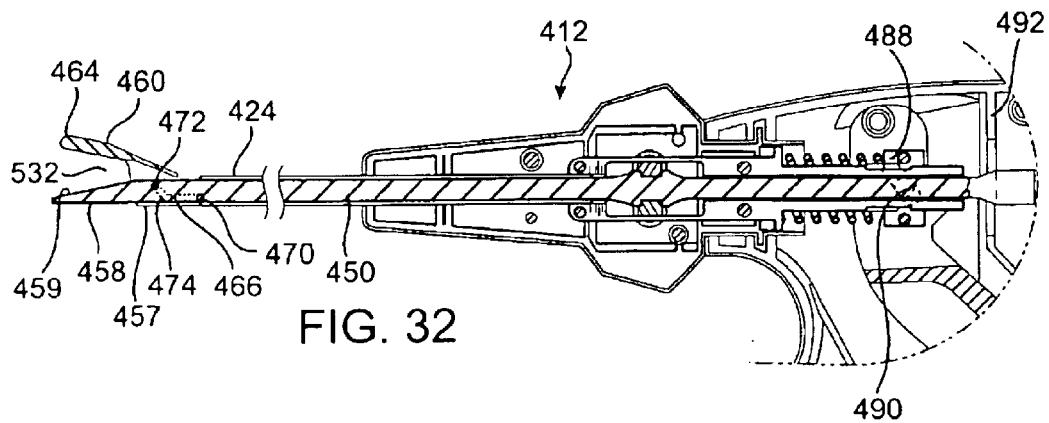
FIG. 32 is an enlarged view of the indicated area of detail of FIG. 31 illustrating the clamp in the open position.
Figure 33:
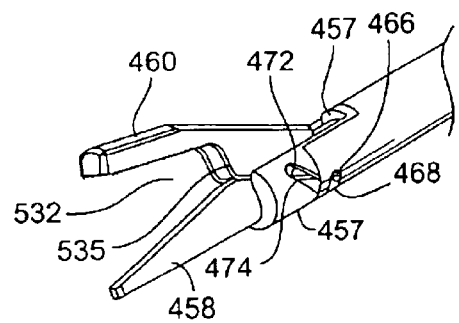
FIG. 33 is a side perspective view of the distal end of the elongated body portion of the ultrasonic instrument shown in FIG. 33.
Figure 34:
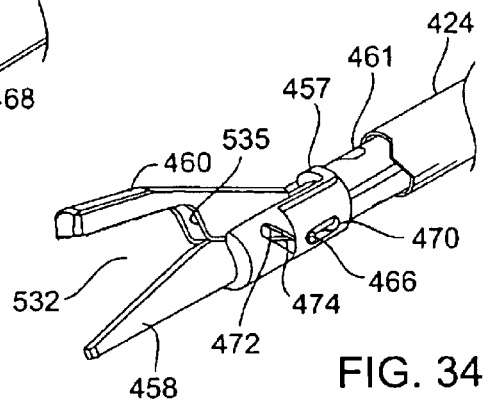
FIG. 34 is a side perspective, partial cutaway view of the distal end of the elongated body portion of the ultrasonic instrument shown in FIG. 33.

Rotation knob 434 is preferably formed from molded half-sections 434a and 434b and includes a proximal cavity 510 for slidably supporting coupling member 498 and a distal bore 512 dimensioned to receive outer tube 442. An annular groove 514 formed in bore 512 is positioned to receive annular flange 444 of outer tube 442. The outer wall of knob 434 has a proximally located annular ring 516 dimensioned to be rotatably received within annular slot 518 formed in housing 422, and a scalloped surface 522 to facilitate gripping of rotatable knob 434. Annular ring 516 permits rotation of knob 434 with respect to housing 422 while preventing axial movement with respect thereto. A pair of rods or pins 524 extend between half-sections 434a and 434b through a rectangular opening 526 formed in coupling member 498. Rods 524 engage a pair of flattened surfaces 528 formed on vibration coupler 450, such that rotation of knob 434 causes rotation of vibration coupler 450 and thus rotation of blade 458 and clamp 460. Alternately, to provide additional surface contact, instead of pins 524, a C-clip shown generally as 580 in FIG. 31A is provided. C-clip 580 mounted by pins 586 has an opening 582 to receive the vibration coupler 450. The flats of vibration coupler 450 contact the four flat regions 590 of the C-clip 580.

A retainer ring (not shown) may be mounted on ribs 492 of housing 422 to provide additional support for actuator tube 446. In this embodiment, tube 446 would extend proximally past ribs 492.

FIGS. 31–34 illustrate ultrasonic instrument 412 with clamp 460 in the open position. The elongated body 424 which includes clamp 460 and blade 458, and housing 422 which includes handles 428 and 436, are packaged as an integral unit that requires no assembly by the user prior to use, i.e., vibration coupler 450, clamp 460, and blade 458 are non-detachably connected. That is, the user needs only to attach transducer 430 to housing 422 to ready instrument 412 for use. In the open position, movable handle 436 is spaced rearwardly from stationary handle portion 428 and protrusions 490 are positioned in the lower proximal portion of cam slots 488. At the distal end of ultrasonic instrument 412, pivot members 466 are positioned near the distal end of guide slots 470 and camming members 472 are positioned in the upper distal portion of cam slots 474. Tissue contact surface 464 of clamp 460 is spaced from blade surface 459 to define a tissue receiving area 532. The proximal end of tissue receiving area 532 is defined by a pair of tissue receiving stops 535 which are preferably integrally formed with clamp 460 and extend below blade surface 459. Preferably, the distal end of blade 458 is devoid of sharp edges which may cause inadvertent damage to tissue during use of instrument 412. Alternately, the distal end of blade 458 may be formed having any shape which may be suitable to a particular surgical application, i.e., flat, pointed, etc.

Figure 35:
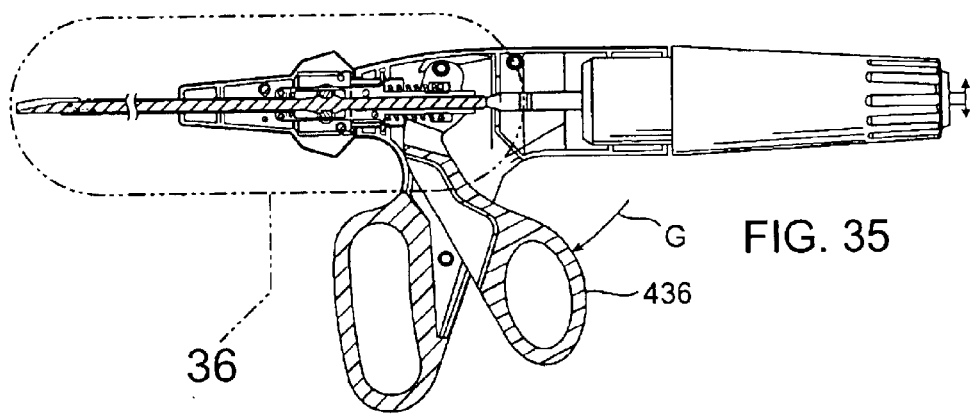
FIG. 35 is a side partial cross-sectional view of the ultrasonic instrument of FIG. 26 in the closed position.
Figure 36:
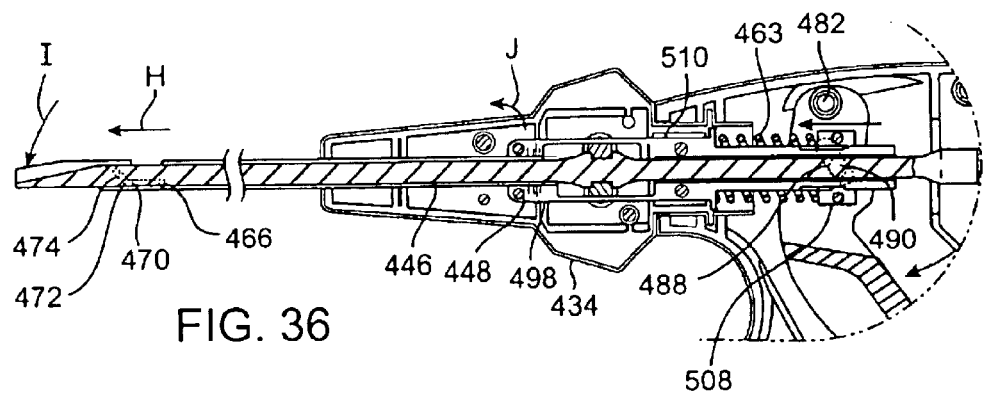
FIG. 36 is an enlarged view of the indicated area of detail of FIG. 35 illustrating the clamp in the closed position.

Referring to FIGS. 35 and 36, when movable handle 436 is pivoted clockwise about pivot member 482 towards stationary handle portion 428, in the direction indicated by arrow "G" in FIG. 35, cam slot 488 engages protrusion 490 of swivel member 508 to advance coupling member 498 distally within cavity 510 of rotation knob 434. Since actuator tube 446 is attached to coupling member 498 by annular flange 448, actuator tube 446 is also advanced distally in the direction indicated by arrow "H" in FIG. 36. Movement of actuator tube 446 distally causes cam slots 474 to move into engagement with camming members 472 to pivot clamp body 462 about pivot members 466, in the direction indicated by arrow "I" in FIG. 36, to move clamp member 462 and tissue contact member 464 into the clamped position. Spring 463 prevents over clamping of tissue by permitting relative movement between swivel member 508 and coupling member 498 after a predetermined clamping pressure has been applied against blade 458. In the clamped position, protrusions 490 are located in a central portion of cam slots 488, pivot members 466 are located near the proximal end of guide slots 470, and camming members 472 are located in the proximal lower portion of cam slots 474.

Elongated body portion 424 can be freely rotated with respect to housing 422 by rotating rotation knob 434. Rotation of knob 434 in the direction indicated by arrow "f" causes rotation of jaw assembly 432 in the direction indicated by arrow "K". Knob 434 is positioned adjacent housing 422 to facilitate one handed operation of both movable handle 436 and rotation knob 434.

Returning to FIGS. 10–19, note that in the example of instrument 80 of FIGS. 10–19, ultrasonic probe 85 is a distinct part separate from actuator rod 11, the probe 85 being arranged to be rotatable about its axis, but is not required to translate along the axis. Rod 111 is arranged to reciprocate axially, and is coupled to gripper 82 to open and close the gripper.

In reference to FIGS. 20–25, in the alternative instrument example 300, the ultrasonic probe assembly 320 is arranged to be axially movable within the instrument along the instrument axis 311, so that the distal portion 322 of the probe assembly 320 is movable in a reciprocating manner within the shaft sheath 312. The probe assembly distal portion 322 is in turn mechanically coupled to a gripper element of the end effector. For example, see actuator tube 446 which engages gripper or clamp 460, shown in FIG. 27.

Figure 20:
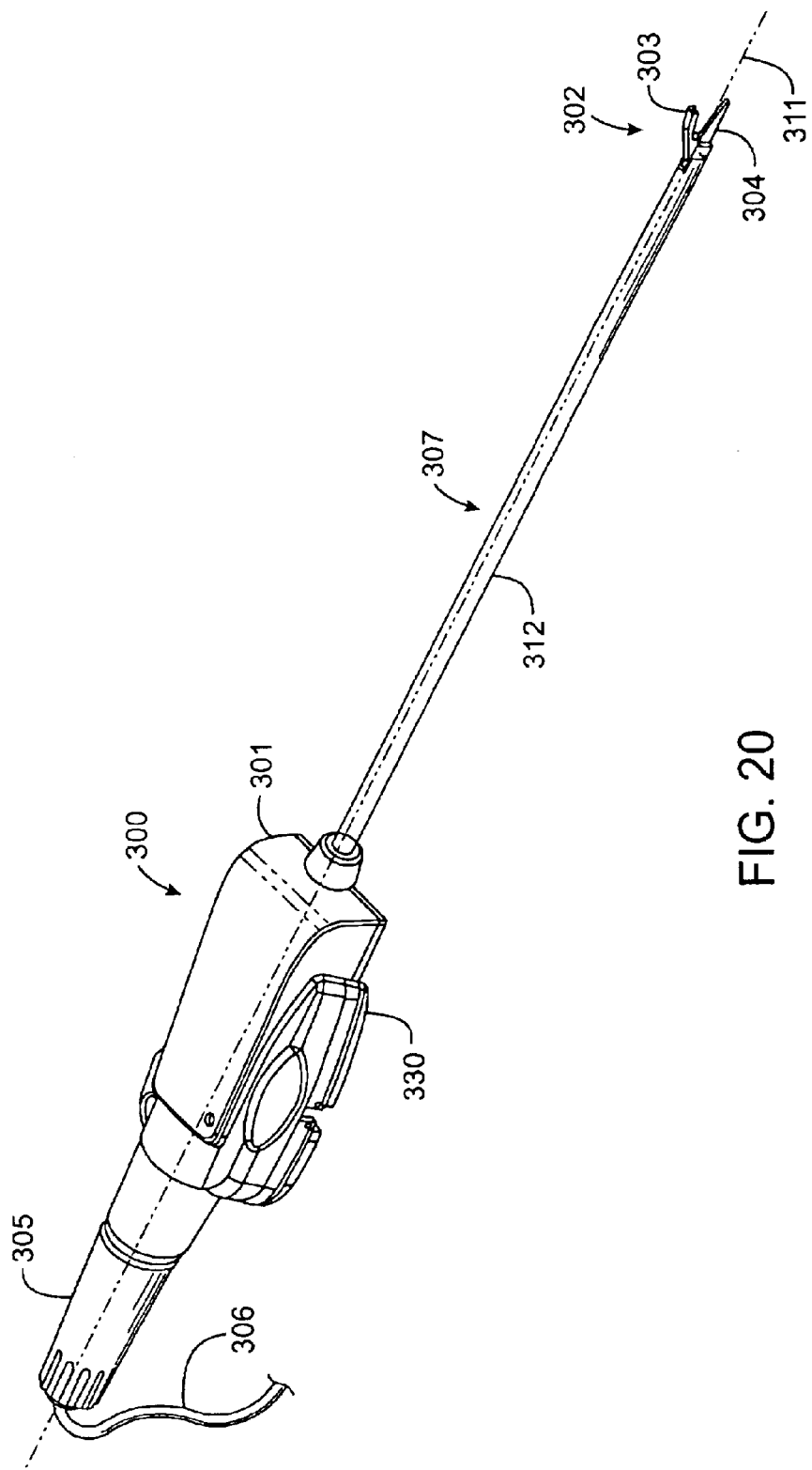
FIG. 20 illustrates an alternative example of an instrument including aspects of the invention.

FIG. 20 illustrates an alternative instrument embodiment 300 including aspects of the invention. The proximal potion comprises an instrument base 330 and a cover 301. Shaft 307 extends distally, covered by outer sheath 312. An end effector 302 is coupled to the distal end of the shaft 307, comprising an ultrasonic blade 304, which cooperatively mates with pivotally mounted gripper or clamp 303. Ultrasonic transducer 305 mounts to the proximal end of base 330, the power/control cable 306 extending to a conventional ultrasonic surgical generator, such as the Auto Sonix* generator (not shown) made by United States Surgical Corporation of Norwalk, Conn.

Figure 21:
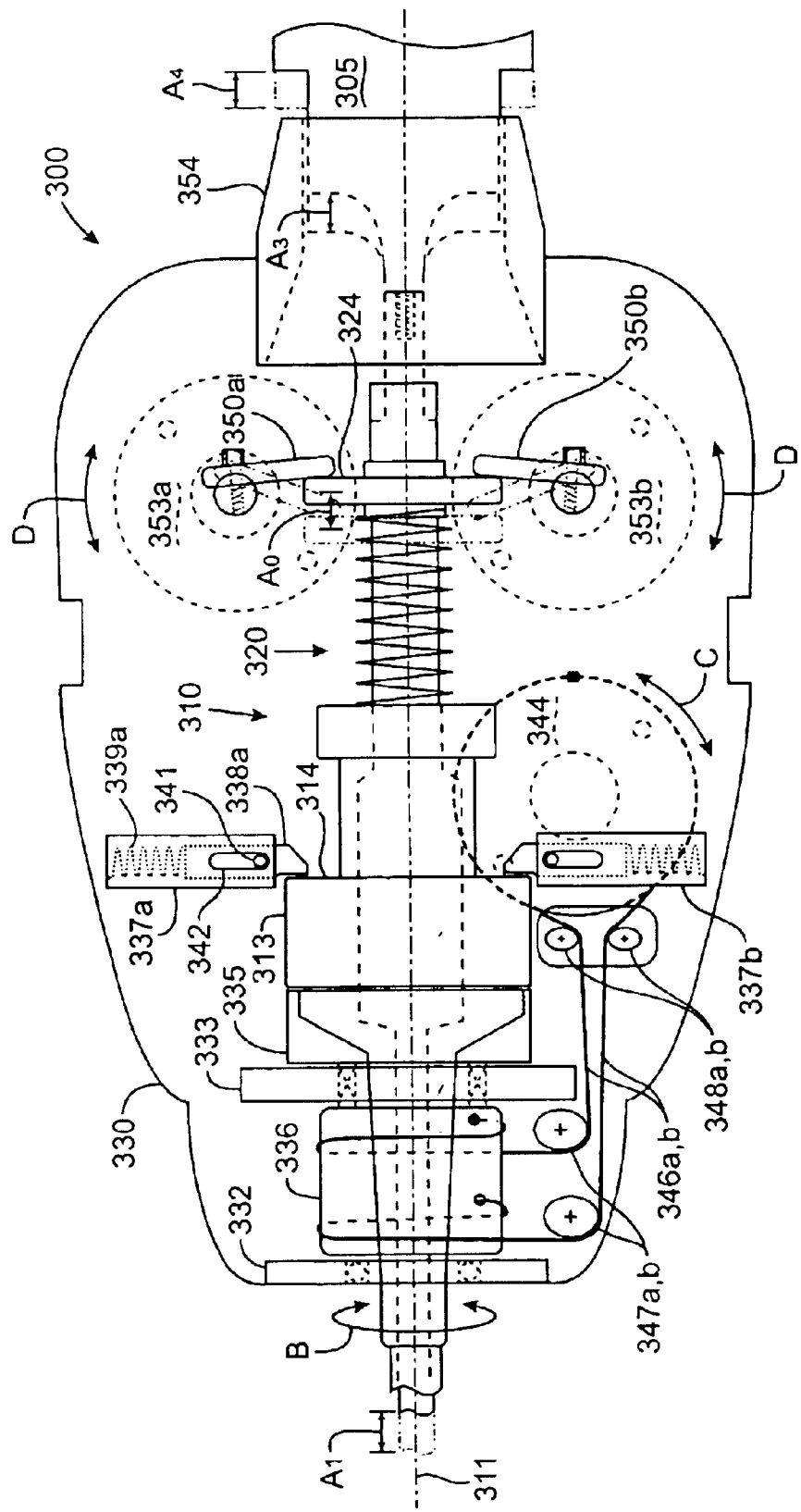
FIG. 21 is a top view of a proximal portion of the alternative instrument embodiment shown in FIG. 20.
Figure 22:
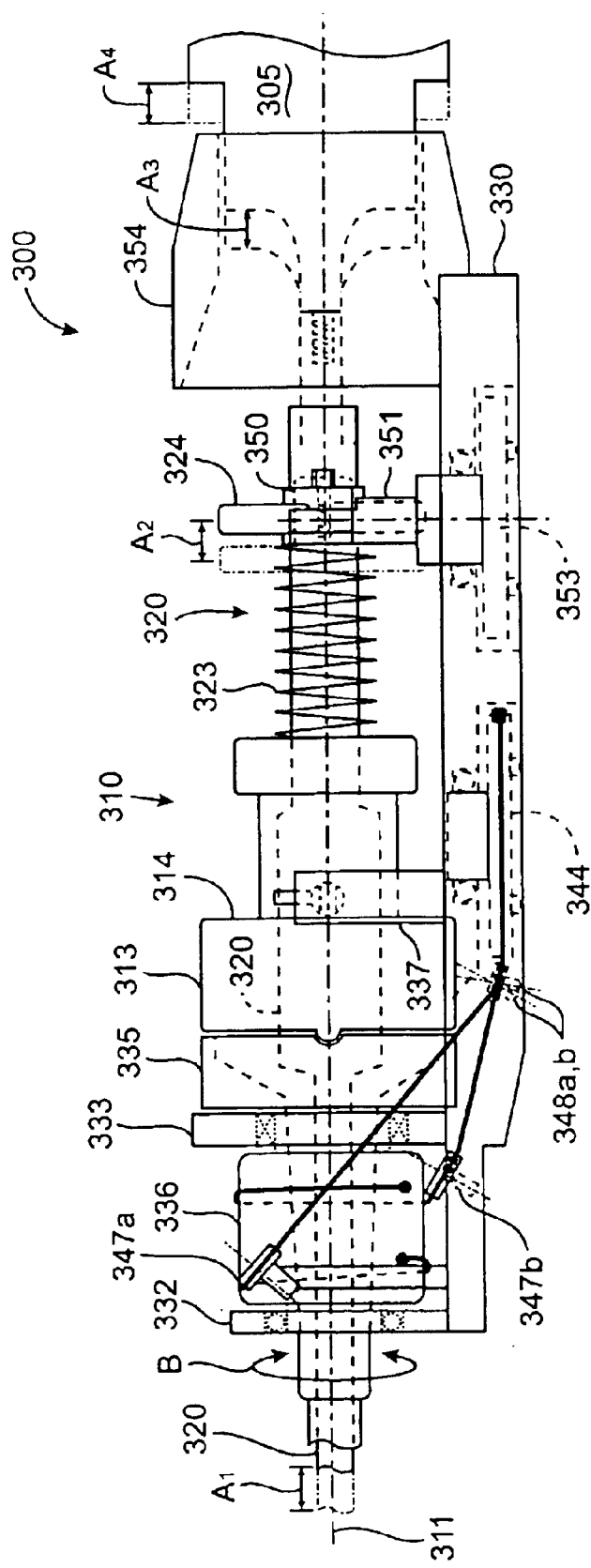
FIG. 22 is a side view of the proximal portion shown in FIG. 21.

FIGS. 21 and 22 are top and side views respectively of the proximal portion of the alternative instrument embodiment 300, illustrated with the cover 301 removed from the base 330. The base 330 supports a rotational support structure including, in this example, front bearing support 332 and medial bushing 333. Bearing 332 and bushing 333 are axially aligned and rotatably mount receiver 335, which spans between bearing 332 and bushing 333. Receiver 335 mounts roll drum 336. Receiver 335 has a hollow axial lumen 340 which is configured to removably mount the treatment assembly 310 (see also FIG. 23). The removable treatment assembly 310 is generally aligned parallel with the axis 311, and is mounted by insertion into lumen 340.

The removable treatment assembly 310 is retained in its mounted position by a latching mechanism, which in the example shown includes a pair of latches 337a and 337b mounted to base 330. The latches 337a and 337b each include a spring-loaded slidable finger 338a, 338b, oriented generally perpendicular to the axis 311. Fingers 338a and 338b are urged by springs 338a and 338b towards the axis 311 by springs 339a and 339b, the fingers overlapping adaptor 313 to bear on rear-facing surface 314 of adaptor 313, thus securing the treatment assembly 310 by preventing axial motion of the adaptor 313 relative to the receiver 335. For insertion or removal of the treatment assembly, the latch fingers 338a and 338b may be retracted by moving the finger against spring forces. In the example shown, for example shown, finger extension 341 protrudes upwardly through slot 342, permitting the finger to be manually retracted. The fingers do not interfere with rotational motion of the receiver and treatment assembly combination about axis 311.

Other conventional latching mechanisms known in the mechanical arts may be used to secure the treatment assembly 310 to the receiver 313. For example, a latching mechanism may be included in the receiver 335, removably coupling to adaptor 313. Alternatively, the contact surface between the receiver lumen 340 and the adaptor 313 may be configured as a threaded joint, to allow disassembly.

The roll barrel 336 of instrument 300 functions in generally the same manner as the roll barrel of instrument 80 shown in FIGS. 10–19. A robotic surgical system interface member (not shown herein, see incorporated U.S. application Ser. Nos. 09/398,958 and 09/418,726, referenced above) is configured to engages the pivotally mounted instrument roll interface member 344 so as to controllably rotate interface member 344 in either direction through a selected range of motion. The instrument roll interface member is supported by bearing 345 mounted to base 301. The perimeter of instrument interface member 344 is shown configured to provide a spool surface 345 which engages cable 346. In the example shown, cable 346 is guided by front and rear idler pulley pairs 347a,b and 348a,b respectively, to conduct the cable 346 to engage the perimeter of roll drum 336. The two ends of cable 346 (346a,b) are led to an upper and lower point on the perimeter of drum 336 respectively, wrapping about the drum 336 in opposite directions, so that rotational motion of interface member 344 (Arrow C) causes the cable to impart a rotational motion to the drum 336, and in turn to impart a corresponding rotational motion to the receiver and treatment assembly, as shown by Arrow B.

Alternatively, a separate roll spool may be axially coupled with instrument interface member 344, in the manner shown in the instrument 80 of FIGS. 10–19. In the example shown, the cable 346 is fixed to the interface member 344 at a medial anchor point 349, the ratio of the diameters of the member 344 and the drum 336 being selected to provide a desired range of rotational motion of drum 336 within less than a 360° rotation of member 344. Alternatively, the cable 346 may be frictionally engaged to member 344 rather than, so as to permit a greater than less than a 360° rotation of member 344. In still another alternative, to separate cables may be attached to two separate spool members. In a still further alternative, a gear train or other mechanical transmission means, e.g., a right-angled helical gear pair, may be used to rotationally couple the interface member 344 with the receiver 335.

It should also be noted that in the instruments examples of the invention shown in FIGS. 10–25, where a mechanical robotic actuator interface is described (see the incorporated U.S. application Ser. Nos. 09/398,958 and 09/418,726, referenced above), other actuation interface devices, such a as an electromechanical drive, a magnetic interface, a flexible drive interface, hydraulic interface or the like, may be substituted without departing from the spirit of the invention. For example, one or more electric motor assemblies or motor packs (optionally having gears and/or encoders) may be mounted to base 330 to drive one or more of the rotational and/or translational degrees of freedom of the instrument, the motor packs being electrically connected to receive control/power signals from (and optionally transmit feedback signals to) the robotic surgical control system.

Figure 23:
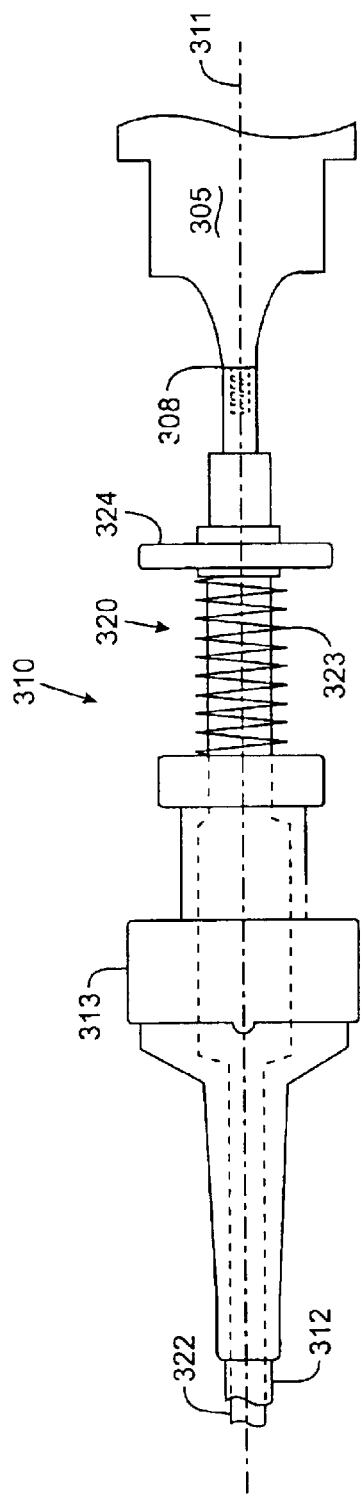
FIG. 23 is a side view of the removable treatment assembly of the instrument embodiment shown in FIG. 20.
Figure 24:
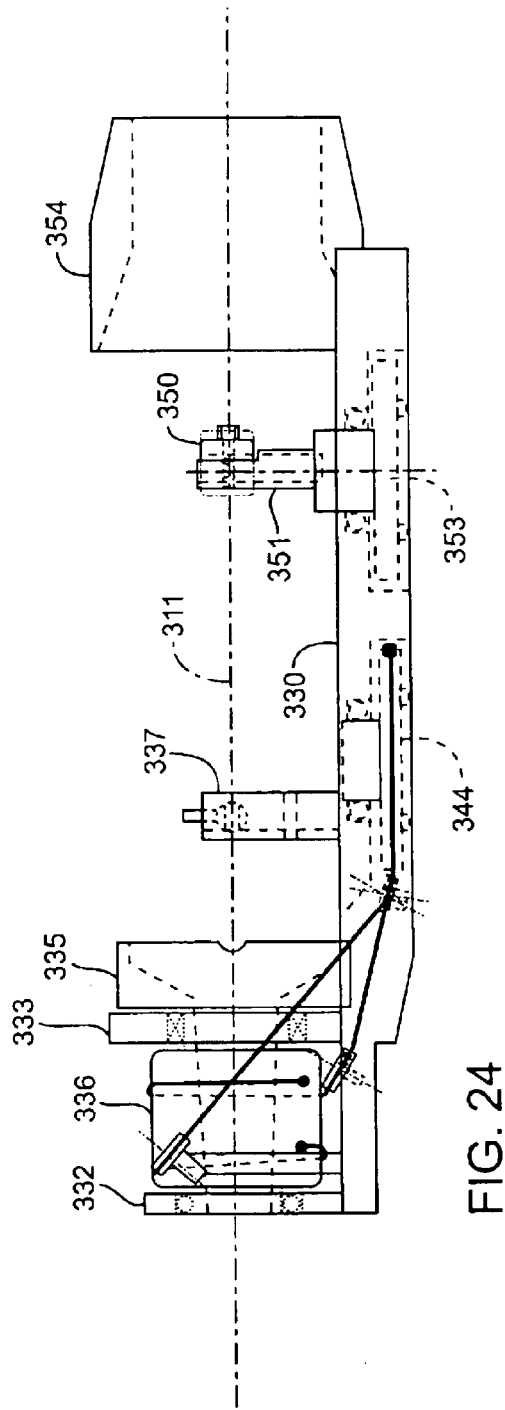
FIG. 24 is a side view of the proximal portion of the instrument embodiment shown in FIG. 22, with the treatment assembly removed.

FIG. 23 is a side view of the removable treatment assembly 310 of the instrument embodiment 300 shown in FIGS. 20 and 21. FIG. 24 is a corresponding side view of the proximal portion of the instrument embodiment 300 from the same perspective as shown in FIG. 22, with the treatment assembly 310 removed.

As shown in FIGS. 21 through 24, the removable treatment assembly 310 comprises adaptor housing 313 having an internal hollow volume 315 communicating between openings at its distal and proximal ends. FIG. 25 is a perspective view of a molded half portion of the adaptor housing 313a of the removable treatment assembly 310 shown in FIGS. 21 and 22.

The interior of housing half portion 313a of the adaptor housing 313 defines half of the internal volume 315, here denoted as 315a. Internal volume 315 holds and mounts the ultrasound conducting core assembly 320. The internal volume 315 is shaped and sized so as to permit the core assembly 320 to move axially through a selected range of motion, as shown by Arrows A in FIGS. 21 and 22. Return spring 323 is mounted between the proximal face 316 of receiver 313 and push plate 324, which is mounted at a medial position on the core assembly 310. Spring 323 serves to bias the location of core assembly 320 to the proximal extent of the range of motion shown by Arrows A1–4.

The adaptor housing mounts the outer sheath 312, which may comprise a tubular structure, such as the outer tube 442 identified in FIG. 29. As shown in the example of FIG. 25, adaptor housing 313 has a distal annular groove 316 which is configured receive the proximal flange of outer tube 442 of FIG. 29.

The core assembly 320 includes components corresponding in function and general structure to the following components described in U.S. Pat. No. 6,280,407 and identified in FIGS. 29 and 30: Coupling member 498; actuator tube 446; vibration coupler 450 and blade 458. The grip or clamp end effector 303 may comprise the component identified as clamp 460 in FIG. 29. The coupling of the end effector and shaft components may be in the manner described in U.S. Pat. No. 6,280,407. The removable treatment assembly comprises a conventional ultrasound transducer 305, preferably coupled to the ultrasonic core assembly by threaded connector, such as the transducer 430 shown in FIG. 29.

As shown in FIGS. 21 and 22, push plate 324 is activated by contact with one or more movable paddle plates 350 (a opposed pair of paddle plates 350a and 350b are shown). Each paddle plate 350 is supported by a generally vertically oriented paddle shaft 351, which is offset laterally from the instrument axis 311. Each paddle 350 extend towards the axis 311 to slightly overlap the perimeter of push plate 324 along the proximal surface of the pushplate. The paddle shafts 351a and 351b are pivotally mounted to base 301, being supported by bearings 352a and 352b respectively, and each is activated by instrument actuator interface member 353a and 353b respectively. Like the instrument roll interface member 344 described above, the instrument actuator interface member 353 is configured to engage a robotic surgical system interface member (not shown herein, see incorporated U.S. application Ser. Nos. 09/398,958 and 09/418,726, referenced above).

As each paddle shaft is rotated (Arrow D), the respective paddle plate pushes against the pushplate 324 (clockwise as shown in FIG. 21 for paddle 350a, counterclockwise as shown for paddle 350b), causing the pushplate to move distally as shown by Arrow A2, in turn causing the core assembly 320 to translate distally as shown by Arrows A1, A3 and A4. The paddles thus actuate the core assembly 320 against the bias force of spring 323. Actuation of the paddles in the opposite direction releases the contact force of the paddles 350 against the pushplate 324, permitting the core assembly 320 to move proximally (to proximal extent of Arrows A1–4). Note that the transducer 305 core assembly 320 is slidingly supported by guide tube 354.

Through the coupling of the core assembly to the grip 303 (see example of FIGS. 26–36, a reciprocating actuation of paddle shafts 351 causes the grip or claim 303 to alternately open and close. In the example shown, the coupling of the grip or clamp 303 is such that the grip is closed and in contact with blade 304 when the core assembly is in its proximal position (proximal extent of Arrows A1–4) as urged by bias spring 323. Thus the grip arrangement is "normally closed", and positive actuation is used to move the core assembly distally to open the grip. Alternatively, the grip coupling may be configured to be "normally open" or neutral.

The materials of the surface of paddles 350 and pushplate 324 may be selected to have a low frictional coefficient, so that sliding contact of the surfaces permits the treatment assembly to be rotated about axis 311 (by engagement of the pivotally mounted instrument roll interface member 344) when the grip 303 is in either an open position or a closed position. The paddles 350 may be biased by a torsion spring or like member to have a clearance from pushplate 324 when actuator torque of the robotic system is not being applied to the actuation interface member 353.

While the above is a complete description of the preferred embodiments of the invention, various alternatives, modifications and equivalents may be used. Therefore, the above description should not be taken as limiting the scope of the invention which is defined by the appended claims.

What is claimed is:

1. A surgical instrument, for use with a robotic surgical system, the robotic surgical system providing master-slave telesurgery in response to input from a surgeon, the surgical instrument comprising:
   an elongate shaft having a proximal end and a distal end, the elongate shaft including an ultrasound probe;
   an end effector disposed at the distal end, the end effector including an ultrasound probe tip of the ultrasound probe; and
   a base disposed at the proximal end for removably connecting the surgical instrument to the robotic surgical system;
   wherein the elongate shaft is configured to rotate in relation to the base about an axis drawn from the proximal end to the distal end; and
   wherein the base includes:
      at least two shafts rotatably mounted to the base, each of the shafts having two ends, at least one of the ends of one of the shafts disposed to engage a corresponding interface member on the robotic surgical system;
      at least two spools, each spool being mounted on one of the shafts;
      at least one cable for connecting two of the spools; and
      a rotating member coupled to the cable and to the elongate shaft, the rotating member being configured to rotate the elongate shaft in response to movements of the interface member, the at least two shafts, the at least two spools and the at least one cable.

2. A surgical instrument as in claim 1, wherein the base further comprises an ultrasound source connector for connecting the ultrasound probe to an external ultrasound source.

3. A surgical instrument as in claim 1, wherein the base further comprises an internal ultrasound source for providing ultrasound energy to the ultrasound probe.

4. A surgical instrument as in claim 1, wherein the ultrasound probe further comprises:
   an ultrasound transducer for generating ultrasonic vibrations; and
   at least one amplifying horn for amplifying the ultrasonic vibrations.

5. The surgical instrument of claim 1, wherein the base comprises a latch mechanism that permits quick connection and disconnection with the robotic surgical system.

6. The surgical instrument of claim 5, wherein the latch mechanism comprises at least two latches.

7. The surgical instrument of claim 6, wherein each latch comprises a retractable finger.

8. The surgical instrument of claim 7, wherein the retractable finger is a spring-loaded slidable finger.

9. A surgical instrument for use with a robotic surgical system, the robotic surgical system providing master-slave telesurgery in response to input from a surgeon, the surgical instrument comprising:
   an elongate shaft having a proximal end and a distal end, the elongate shaft including an ultrasound probe;
   an end effector disposed at the distal end, the end effector including:
      an ultrasound probe tip of the ultrasound probe; and
      a gripping member hingedly attached to the end effector for gripping tissue in cooperation with the ultrasound probe tip;
   at least one force transmitting member for transmitting one or more forces between the robotic surgical system and the gripping member to move the gripping member; and
   a base disposed at the proximal end for removably connecting the surgical instrument to the robotic surgical system;
   wherein the elongate shaft is configured to rotate in relation to the base about an axis drawn from the proximal end to the distal end; and
   wherein the at least one transmitting member comprises:
      at least two shafts rotatably mounted to the base, each of the shafts having two ends, at least one of the ends of one of the shafts disposed to engage a corresponding interface member on the robotic surgical system;
      at least two spools, each spool being mounted on one of the shafts;
      at least one cable for connecting two of the spools; and
      an actuator rod coupled to the cable and to the gripping member and extending through the elongate shaft, the actuator rod being configured to move the gripping member in response to movements of the interface member, the at least two shafts, the at least two spools and the at least one cable.

10. A surgical instrument for use with a robotic surgical system, the robotic surgical system providing master-slave telesurgery in response to input from a surgeon, the surgical instrument comprising:
   an elongate instrument probe assembly having a proximal end and a distal end, the distal end insertable through a minimally invasive surgical incision into the body of a patient; and
   an instrument base coupled to the instrument probe assembly adjacent the proximal end, the instrument base comprising an instrument interface assembly removably connectable to the robotic surgical system and engagable with at least one interface actuator of the robotic surgical system so as to receive at least one input actuation, the interface assembly being coupled to the instrument probe assembly so as to move at least a portion of the instrument probe assembly in at least one degree of freedom;
   wherein the instrument base comprises:
      at least two shafts rotatably mounted to the base, each of the shafts having two ends, at least one of the ends of one of the shafts disposed to engage a corresponding interface member on the robotic surgical system;
      at least two spools, each spool being mounted on one of the shafts;
      at least one cable for connecting two of the spools; and
      a rotating member coupled to the cable and to the elongate shaft, the rotating member being configured to rotate the elongate shaft in response to movements of the interface member, the at least two shafts, the at least two spools and the at least one cable.

11. The surgical instrument of claim 10, further comprising an end effector coupled to the instrument probe assembly adjacent the distal end, the end effector having at least one end effector member configured to engage tissue employing a medical energy modality.

12. The surgical instrument of claims 11, wherein:

the surgical instrument further comprises at least one energy connector device engageable to operatively communicate with a medical energy system; and the instrument probe assembly further comprises at least one energy conduction element operatively coupled to the energy connector device and extending between the proximal end and the distal end, the conduction element coupled to the end effector member to communicate the medical energy modality to the engaged tissue.

13. The surgical instrument of claim 12, wherein the medical energy modality is ultrasound treatment energy.

14. The surgical instrument of claim 12, wherein the medical energy modality is ultrasound diagnostic energy.

15. The surgical instrument of claim 12, wherein the medical energy modality is electrosurgical treatment energy.

16. The surgical instrument of claim 12, wherein the instrument probe assembly includes an ultrasonic treatment probe assembly, and the medical energy modality is ultrasound treatment energy.

17. The surgical instrument of claim 12, wherein:

the instrument probe assembly further comprises an ultrasonic transducer coupled to the energy connection device, the energy connection device operatively connectable to a surgical ultrasound generator, the conduction element further comprises an ultrasonic conduction core coupled to the transducer, and the end effector member further comprises an ultrasonic treatment probe tip coupled to the ultrasonic conduction core and configured to engage tissue to transmit ultrasonic energy to the engaged tissue.

18. The surgical instrument of claim 17, wherein the instrument probe assembly further comprises at least one grip drive element extending between the distal end and the proximal end and coupled to the interface assembly, the interface assembly being configured to move the drive element in response to the at least one actuation input; and the end effector further comprises a grip member pivotally coupled adjacent the ultrasonic treatment probe tip, the grip member coupled to the drive element so as to pivot in response to movement of the drive member to be closeable against the probe tip so as to engage tissue therebetween.

19. The surgical instrument of claim 17, wherein:

at least a distal portion of the instrument probe assembly including the end effector defines an elongate instrument shaft portion extending distally from the instrument base, at least the instrument shaft portion of the instrument probe assembly being coupled to the instrument base so as to be rotatable about a instrument axis;

the instrument includes at least one shaft drive element coupled to the interface assembly, the interface assembly being configured to move the shaft drive element in response to the at least one actuation input; and the shaft drive element being coupled to at least the instrument shaft portion of the instrument probe assembly so as to cause at least the instrument shaft portion to rotate about the instrument axis in response to movement of the shaft drive element.

\* \* \* \* \*